(12) United States Patent
Lowe et al.

(10) Patent No.: US 10,261,077 B2
(45) Date of Patent: *Apr. 16, 2019

(54) MICROFLUIDICS BASED ASSAY DEVICE

(71) Applicant: LUMIRADx UK LTD., London (GB)

(72) Inventors: Phillip Lowe, Tullibody (GB); Steven Alexander Keatch, Stirling (GB); Brian McGuigan, Stirling (GB)

(73) Assignee: LUMIRADX UK LTD, London (GB)

( * ) Notice: Subject to any disclaimer, the term of this patent is extended or adjusted under 35 U.S.C. 154(b) by 16 days.

This patent is subject to a terminal disclaimer.

(21) Appl. No.: 15/155,594

(22) Filed: May 16, 2016

(65) Prior Publication Data

US 2016/0320374 A1 Nov. 3, 2016

Related U.S. Application Data

(63) Continuation of application No. 13/983,650, filed as application No. PCT/GB2012/000122 on Feb. 7, 2012, now Pat. No. 9,341,620.

(30) Foreign Application Priority Data

Feb. 7, 2011 (GB) .................................. 1102037.7

(51) Int. Cl.
  *G01N 33/543* (2006.01)
  *C12Q 1/00* (2006.01)
  (Continued)

(52) U.S. Cl.
  CPC .... *G01N 33/5438* (2013.01); *B01L 3/502715* (2013.01); *B01L 3/502761* (2013.01);
  (Continued)

(58) Field of Classification Search
  CPC ........... G01N 33/5438; G01N 27/3277; G01N 33/54326; G01N 33/54366;
  (Continued)

(56) References Cited

U.S. PATENT DOCUMENTS 4,098,876 A 7/1978 Piasio et al.
4,772,550 A 9/1988 Greenquist
(Continued)

FOREIGN PATENT DOCUMENTS

CN 101553729 A 10/2009
CN 201596509 U 10/2010
(Continued)

OTHER PUBLICATIONS

Bange, Adam, et al., "Microfluidie Immunosensor Systems", 2005, Biosensors and Bioelectronics, No. 20, pp. 2488-2503.
(Continued)

*Primary Examiner* — Melanie Brown
(74) *Attorney, Agent, or Firm* — Goodwin Procter LLP

(57) ABSTRACT

A subtractive corrective assay device and methodology, whereby ail required binding and label detection reagents are initially located within the detection zone. Application of a magnetic field is used to selectively remove bound label from the detection zone by means of paramagnetic particles. The relationship between measured label concentration before and after the application of a magnetic field within the detection zone is used to accurately measure analyte concentration within the sample.

12 Claims, 26 Drawing Sheets

(51) Int. Cl.
*B01L 3/00* (2006.01)
*G01N 27/327* (2006.01)

(52) U.S. Cl.
CPC .............. *C12Q 1/001* (2013.01); *C12Q 1/006* (2013.01); *C12Y 101/03004* (2013.01); *G01N 27/3277* (2013.01); *G01N 33/54326* (2013.01); *G01N 33/54366* (2013.01); *B01L 2200/04* (2013.01); *B01L 2200/0647* (2013.01); *B01L 2200/16* (2013.01); *B01L 2300/0645* (2013.01); *B01L 2300/0864* (2013.01); *B01L 2300/161* (2013.01); *B01L 2400/043* (2013.01); *B01L 2400/0688* (2013.01); *G01N 2333/904* (2013.01)

(58) Field of Classification Search
CPC ......... B01L 3/502715; B01L 3/502761; C12Y 101/03004; C12Q 1/006; C12Q 1/001
See application file for complete search history.

(56) References Cited

U.S. PATENT DOCUMENTS

| | | | |
|---|---|---|---|
| 5,145,784 | A | 9/1992 | Cox et al. |
| 5,674,681 | A | 10/1997 | Rothenberg |
| 5,698,448 | A | 12/1997 | Soldin |
| 5,939,272 | A | 8/1999 | Buechler et al. |
| 6,225,043 | B1 * | 5/2001 | Abuknesha .......... G01N 33/537 435/283.1 |
| 6,299,757 | B1 | 10/2001 | Feldman et al. |
| 2007/0031283 | A1 | 2/2007 | Davis et al. |
| 2008/0199893 | A1 | 8/2008 | Neubert et al. |
| 2009/0130771 | A1 | 5/2009 | Davies et al. |

FOREIGN PATENT DOCUMENTS

| | | |
|---|---|---|
| GB | 2436616 A | 10/2007 |
| GB | 2443694 A | 5/2008 |
| JP | 2006377221 | 1/2006 |
| JP | 2009540326 A | 11/2009 |
| JP | 2010509581 A | 3/2010 |
| WO | WO-2007110779 A2 | 10/2007 |
| WO | WO-2008007242 A2 | 1/2008 |
| WO | WO-2008056165 A1 | 5/2008 |

OTHER PUBLICATIONS

Kurita, Ryoji, et al., "On-Chip Enzyme Innunoassay of a Cardiac Marker Using a Microfluidic Device Combined with a Protable Surface Plasmon Resonance System", 2006, Anal. Chem., No. 78, pp. 5525-5531.

Lim, C.T., et al.,"Bead-Based Microfluidic Immunoassays: The Next Generation", 2007, Biosensors and Bioelectronics, No. 22, pp. 1197-1204.

Meagher, Robert J., et al., "An Integrated Microfluidic Platform for Sensitive and Rapid Detection of Biological Toxins", 2008, Lab. Chip, No. 8, pp. 2046-2053.

PCT Search Report and Written Opinion for PCT/GB2012/000122, completed May 24, 2012.

Peoples, Michael C., et al., "Microfluidic Immunoaffinity Separations for Bioanalysis", 2008, Journal of Chromatography, No. 866, pp. 14-25.

* cited by examiner

Figure 21

| PSA (ng/ml) | Delta Post i/A-Pre i/A | | |
|---|---|---|---|
| | Mean | sd | cv |
| 0 | 4.57E-07 | 7.07E-10 | 0.154897 |
| 4 | 4.22E-07 | 1.82E-08 | 4.324239 |
| 16 | 4.01E-07 | | 0 |
| 250 | 2.62E-07 | 1.5E-08 | 5.734833 |
| 500 | 1.72E-07 | 2E-09 | 1.162791 |
| 1000 | 1.27E-07 | 5.2E-09 | 4.091459 |
| 2000 | 1.07E-07 | 5.77E-09 | 5.37904 |

Figure 23

| PSA (ng/ml) | Post i/A/Pre i/A Ratio | | |
|---|---|---|---|
| | Mean | sd | cv |
| 0 | 3.409425 | 0.048684 | 1.427938 |
| 4 | 3.055042 | 0.018702 | 0.612161 |
| 16 | 2.782222 | | 0 |
| 250 | 2.276892 | 0.097139 | 4.266315 |
| 500 | 1.79398 | 0.016749 | 0.933642 |
| 1000 | 1.680613 | 0.03504 | 2.084929 |
| 2000 | 1.472299 | 0.025735 | 1.747948 |

MICROFLUIDICS BASED ASSAY DEVICE

CROSS REFERENCE TO RELATED APPLICATIONS

This application is a continuation application of U.S. Nonprovisional Patent Application Ser. No. 13/983,650, filed on Sep. 6, 2013, now U.S. Pat. No. 9,341,620, which is a U.S. National Stage Entry Application under 35 U.S.C. § 371(b) of International Application Serial Number PCT/GB2012/000122, filed on Feb. 7, 2012, which claims the benefit of United Kingdom Patent Application Serial No. 1102037.7, filed on Feb. 7, 2011, the disclosures of all of which are hereby incorporated herein by reference in their entireties.

FIELD OF THE INVENTION

The present invention relates to a microfluidic based assay system, comprising a disposable assay cartridge and associated reading device, as well as the individual components themselves. The present invention also relates to methods of conducting assays, using the cartridge and device of the invention, as well as kits for conducting assays.

BACKGROUND TO THE INVENTION

There is a constant need within the IVD industry to deliver improvements in performance. Improvements in performance can include accuracy, precision, cost, multiplexing, total test time etc. The novel subtractive corrective assay device and method described in this document is designed to deliver such improvements. The novel subtractive corrective assay device and method is composed of a single use disposable strip and a reusable reader. Although other detection methodologies are applicable, the preferred embodiment focuses on electrochemical detection.

In the prior art there are numerous examples whereby magnetic particles and associated bound species which give detectable changes are brought to a detection zone via a magnetic field. Typically the unbound label is kept away from the detection zone with the bound label being accumulated within the detection zone and inducing the detectable change.

US 2009/0130771 A1 incorporated by reference in its entirety, describes the use of magnetic particles to capture analyte but accumulates them within a detection zone to measure an increased concentration of analyte within the detection zone. US 2009/0130771 A1 also uses a separate reference zone for any background correction. This only works for correction of background of the sample itself and not for any variations in label or other reagent concentrations as the two areas are different and therefore differences will be present with respect to resuspended reagent concentrations as well as the reproducibility of measuring within 2 distinct areas, such as reference vs detection zone size, opacity etc. U.S. 2009/0130771 A1 does make reference to the possibility of using the detection zone for a background measurement but only when "GOD [label] particles are substantially absent from the detection zone" and therefore does not correct for variation in label concentration.

It is amongst the objects of the present invention to provide a cheap and reliable assay system for carrying out IVD tests.

It is amongst the objects of the present invention to provide an assay cartridge design platform and reader which may be easily and cheaply fabricated, as well as being able to be configured to carry out a specified assay or assays.

It is amongst the objects of the present invention to provide an assay cartridge which may easily be adapted to carry out a variety of different specified assays.

It is amongst the objects of the present invention to provide an assay system comprising a reader which may preferably be used or easily adapted to perform a variety of different assays.

SUMMARY OF THE INVENTION

The present invention is based on the development of a novel subtractive assay device and method whereby all the reagents are initially located within the detection zone. The assay architecture allows for very accurate, sensitive measurements whereby the concentration of the unbound label is used to measure the concentration of the analyte(s).

In a first aspect the present invention provides a microfluidic assay cartridge for use in a subtraction assay for detecting an analyte in a sample of fluid, the cartridge comprising:

a sample port for introducing said fluid sample into the cartridge, a substrate comprising one or more microfluidic channels disposed therein and comprising a binding agent disposed within said channel(s) for binding any of said analyte within the sample and a label for use in detecting an amount of the analyte present in the sample; and a detection area within or wholly comprising an area where analyte and label binding occurs, said detection area from which bound analyte is removed allowing determination of said analyte concentration indirectly by measurement of any remaining unbound label.

The detection zone contains the reagents required for the binding reaction and an enzymatic reaction to occur simultaneously upon rehydration of the reagents by addition of the sample. In a specific embodiment, specifically anti-analyte magnetic particles, anti-analyte glucose oxidase (GOD) label and mediator system are located within the detection zone. Glucose is deposited upstream from the detection zone so upon cartridge filling by the sample, the glucose is rehydrated and presented with sample to the detection zone(s). The sample (with glucose) rehydrates the binding and enzymatic reagents. Immediately both reactions start (formation of bound complexes and enzymatic turnover of substrate). A reference measurement of enzyme turnover is then performed which takes into account a number of variables in the assay (anti-analyte-GOD label concentration, mediator concentrations, working electrode size etc). This reference measurement is dominated by the anti-analyte-GOD label concentration. Hereinafter, this is termed the pre magnetic separation measurement.

After a defined period of time (e.g. 4 minutes) a magnetic field is applied to the strip. As a result the paramagnetic particle-analyte and paramagnetic particle-analyte-label complexes are selectively removed from the detection zone to the source of the magnetic field leaving unbound GOD label in the detection zone. After a defined period of time (e.g. two minutes) a measurement is performed measuring the concentration of the unbound GOD label remaining within the detection zone. The relationship between the label concentration before and after the magnetic separation step is used to determine the concentration of analyte(s) within a sample.

There are a number of advantages to performing a subtraction corrective assay which measures the label concentration before and after the magnetic separation. A great source of variation and inaccuracy within disposable IVD strips is the amount/concentration of reagents deposited in the cartridge. The corrective subtractive assay methodology corrects for this because each of the reagents is deposited within the detection zone allowing determination of label concentration and hence the ability to correct for differences in label concentrations. This works exceptionally well for a subtraction method as only events at a working electrode are being interrogated (i.e. the label concentration at the working electrode is measured and then after the magnetic removal of the bound label, the unbound label concentration at the working electrode is re-measured). In accumulation assays where detectable species are bought to the electrode there is no opportunity for correction, even if each of the reagents were located in the detection area; bound species would still be brought to the working electrode (and hence the inability to correct for variations in label concentration elsewhere in the strip). This does not occur in the corrective subtraction assays of the present invention and therefore it allows very accurate corrections for variations in label concentrations (and other sources of variation previously described) resulting in improved precision, sensitivity, accuracy and overall assay performance (the corrective ability is profound on the assay performance as further described in the detailed description).

An additional major advantage of the subtractive corrective methodology is that of independence of strip volume. In assay methodologies whereby label is brought to the detection zone via magnetic particles the measurement is susceptible to volume changes of the strip (width, height etc) of the channel (i.e. the amount of analyte available for binding varies with the variation of the dimensions of the strip). In the case of the subtractive corrective methodology the volume of the strip is normalised. This is driven by the pre magnetic separation measurement whereby only the species at the working electrode surface is measured. This measurement therefore allows for correction in strip volume as only the sample volume at the working electrodes is measured, therefore variations in strip channel height, strip width, strip volume, electrode size and reagent concentrations can be corrected for resulting in highly accurate results.

Assays using accumulation of paramagnetic particles to bring bound label to a detection area also suffer from difficulties in collecting all (or a reproducible number) of the paramagnetic particles and presenting them to the detector in a reproducible manner (for example paramagnetic particle bead band dimensions) to ensure accurate results. The subtraction methodology does not suffer from this as the paramagnetic particles and bound species are removed from the detection area.

As the assay methodology is very simple it is easy to create cartridge formats capable of multiple measurements. This allows measurements of many different analytes or multiple measurements of the same analytes. In addition the simplicity of the assay allows a highly manufacturable cheap cartridge design that uses very small sample volumes and is therefore applicable to many product applications The cartridge design of the present invention may easily be adapted to carry out a number of different assays and hence can be considered as an assay platform for a variety of assays. The cartridge and channel(s) disposed therein may be formed in any manner of ways known to the skilled addressees, which may include photolithography, wet chemical etching, laser ablation, injection moulding, embossing and printing techniques. However, in a preferred embodiment, the cartridge and the channels and other features disposed therein, are formed by a sandwich of three separate substrates—a top, middle and bottom substrate.

The cartridge can be formed of any suitable material, such as polycarbonate, polyester, polystyrene, PMMA, etc. and the/each substrate may be formed of a single or plurality of material(s). In the embodiment comprising three substrates, the middle substrate comprises a pattern cut through the substrate, corresponding to certain features of the cartridge, such as the channel(s), sample introduction port and the like. By applying and sandwiching (such as by heat sealing, gluing, stapling and the like) appropriately cut top and bottom substrates, to sandwich the middle substrate between the top and bottom substrates, a cartridge can be provided in which channels and other features are disposed. Openings or features in the top and/or bottom substrate may be designed to allow air to vent from the cartridge to allow filling with sample or co-locate with features in a reader device (as will be discussed hereinafter), which may facilitate with correct location of the cartridge in the reader.

As identified, in use, the sample is applied to the cartridge through a sample introduction port such as by way of capillary action. In a preferred embodiment the sample introduction port is an aperture in a side or face of the cartridge. Desirably the cartridge is in the form of a generally thin planar device comprising top and bottom faces and four edges. In this arrangement, the sample introduction port may be formed in one of the edges of the cartridge, so that a user need only contact the sample with the aperture formed in the edge, in order to enable sample uptake into the cartridge. In use the user contacts the fluid sample with the port/aperture and, in certain embodiments, due to the dimensions of said channel(s) within the cartridge, fluid is drawn into the cartridge by capillary action. The dimensions of the sample port/aperture may be smaller or larger than the dimensions of the channel(s).

Said channel(s) in the cartridge may also comprise one or more fluid stop features, which are designed to prevent the sample and/or other fluids from passing through the stop feature, by virtue of capillary action alone. A preferred stop feature is a hydrophobic material (e.g. printable conductive or non conductive inks) or a process or material that changes the surface properties of a channel surface therefore creating a hydrophilic/hydrophobic differential (e.g. by way of laser ablation, surface scoring, surface material removal, evaporated metallic materials etc), which is designed to abut/be a wall feature or is coated on a wall of the channel or an air gap in the channel (for example a hole in the lid and/or base material which spans the channel). In the embodiment where the channels are formed by virtue of three substrates being sandwiched together thereby forming the channels, the hydrophobic material may be applied to the top and/or bottom substrates, such that when the three substrates are sandwiched together, the hydrophobic stop material forms a feature on the top and/or bottom surface of said channel.

As well as the microfluidic channel(s), the cartridge of the present invention may comprise one or more electrode features which contact with the channel and hence the sample once introduced into the cartridge. The electrodes are designed to contact electrical contacts within the reader, enabling a variety of readings to be taken, where appropriate. For example, one or more electrodes in the cartridge may be designed to detect correct loading of the cartridge and the reader may signal to the user whether or not the cartridge has a) been correctly inserted into the reader and/or the sample loaded into the cartridge correctly. The electrode(s) may also carry out one or more electrical measurements on the sample itself. For example, when the sample is a sample of whole blood, the electrode(s) may conduct a hematocrit measurement of the sample, which may be important in determining an accurate concentration of the analyte to be detected. Conductivity and/or impedance measurements may be determined depending on the sample being studied. The label used in analyte detection may be electrochemical (or involved in an electrochemical reaction) and therefore these electrodes may be used in the measurement of the label concentration and therefore analyte concentration. Thus, the cartridges of the present invention may use electrical measurements on the sample for functions such as fill detection, hematocrit measurement and analyte measurement.

Any conductive material could be used to form electrodes. For example screen printable carbon inks, silver/silver chloride inks, gold, platinum, copper etc could be used and applied to a substrate by various means such as screen printing, sputtering, ink jet printing etc or partial removal of electrode material from a substrate by various means including chemical etching, laser ablation etc.

The sample to be applied to the cartridge may be any suitable fluid sample. It may for example be a sample of fluid obtained from a subject, such as a whole blood, plasma, saliva, semen, sweat, serum, menses, amniotic fluid, tears, a tissue swab, urine, cerebrospinal fluid, mucous and the like. It is to be appreciated that the assay systems of the present invention may be applied in the human health area, including large and growing IVD markets (e.g. cancer, cardiology, diabetes and infectious disease). The assays may also be used to test drugs and drug action. However, the system may also be applied in environmental settings where it is desirable to detect, for example toxic agents or infectious agents such as bacteria or viruses. Thus, samples from rivers or lakes or swabs from solid surfaces may be taken in order to obtain a fluid sample for providing to the cartridge. The assay systems may also be utilised for veterinary applications for laboratory, point of care and in the field testing. Essentially any assay in which a sample can be provided in a fluid form may be utilised in the present invention.

The sample may, for instance, include materials obtained directly from a source, such as a sample of whole blood, as well as materials pretreated using techniques, such as filtration, precipitation, dilution, distillation, mixing, concentration, inactivation of interfering agents, etc. These steps may be carried out prior to the sample being introduced to the cartridge or may be carried out by the cartridge itself.

The sample may be introduced prior to the cartridge being inserted into the reader or after the cartridge has been inserted into the reader. The cartridge may be so designed that the sample is introduced by way of capillary action.

The analyte to be detected can be any desired analyte and may include proteins, peptides, antibodies, nucleic acid, microorganisms (such as bacteria and viruses), chemical agents, toxins, pharmaceuticals, metabolites, cellular moieties and the like. For example, the present system may be adapted to detect any type of analyte that can bind a suitable binding agent. The binding agent may be any suitable agent which is able to bind specifically to the analyte to be detected. For example, if the analyte is a protein or peptide, the binding agent may be a receptor or antibody which is capable of specifically binding to the protein/peptide. Conversely an antibody may be bound by a protein/peptide which the antibody is designed to specifically bind to. Nucleic acids may be bound by other nucleic acids which are capable of specifically hybridising to the analyte nucleic acid. Microorganisms may be bound by antibodies which specifically bind to proteins on the surface of the microorganism. Chemical agents, toxins, pharmaceuticals, metabolites may be bound by chemical moieties which are capable or reacting or binding to the aforementioned chemical analytes via appropriate bonding reactions, or affinities. Many types of binding techniques are well known to those of skill in the art.

Moreover, the binding agent may be an enzyme or an enzyme substrate. For example analytes such as glucose through well described enzymatic methodologies may be detected, for example the reaction product formed following the enzyme reacting with the glucose may be detected by using electrochemical, or optical detection techniques known to the skilled addressee. Such measurements can be made as standalone measurements or in combination with other analytes to be detected in the sample.

The binding agent is attached to a magnetic agent, such as a paramagnetic particle by methods including physical adsorption, covalent chemical coupling, non covalent chemical bonding (e.g. biotin-avidin) or any combination of these. In a preferred embodiment, the binding agent is bound to the paramagnetic particle via non covalent chemical bonding (e.g. biotin-avidin association). The paramagnetic agents/particles which are functionalised to comprise the binding agent bound thereto, may simply be deposited within a channel of the cartridge, such that upon the sample being applied to the cartridge and being drawn into the channel(s), the functionalised paramagnetic agents/particles are resuspended by the fluid sample and hence come into contact with any analyte in the sample.

As mentioned above as well as the binding agents, the cartridge may comprise one or more further reagents deposited within said microfluidic channels(s), which reagents may facilitate detection of the captured analyte. For example said one or more reagents may include a label which has been adapted to specifically bind to the captured analyte, thus facilitating its detection. These reagents may be deposited separately or in combination with other reagents, such as functionalised paramagnetic particles.

Further reagents deposited within said microfluidic channel(s) may have functions including but not limited to improving stability of other reagents, improving/controlling resuspension of reagents, preventing coagulation of blood sample, providing a substrate or cofactor required for a enzymatic or chemical reaction, controlling the pH or ionic conditions of sample once applied to the cartridge, enhancing the signal produced by the label, and enzymes which convert the product from a label-induced reaction to a species to be detected by the reader.

Bound analyte may be detected indirectly providing the bound analyte is capable of generating a detectable signal, whereby removal of bound analyte from the detection area will result in a decreased signal, or upon binding of the analyte a reaction may take place, so as to generate a reaction product and after removal of bound analyte from the detection area, the decreased amount of unreacted analyte may be detected. However, in a preferred embodiment, bound analyte is contacted with a label which is able to bind the bound analyte and a label/binding agent/analyte complex is subsequently removed from the detection area and the free unbound label that remains is detected. Typically the label is able to bind to a different portion of the analyte to which the first binding agent binds, or is capable of binding to a region of the binding agent/analyte complex which is formed only on generation of such a complex.

Desirably the binding agent and any detection agent/label are in a dry state when deposited in the channel(s) of the cartridge.

When a capture agent and label (which are designed to facilitate capture and detection of the analyte) are desired, they can be deposited together or separately so they only come together upon rehydration with application of sample. Any other reagents which are desired for the assay can be deposited together with the capture and/or label or separate to either or both of these. In this way, rehydration of reagents can be ordered.

Each cartridge may be designed to carry out single analyte detection or multiple analyte detection. Moreover, each cartridge may comprise more than one microfluidic channel system, so that more than one assay may be carried out using a single cartridge.

Desirably the cartridges may easily be mass produced.

Once the cartridge has been loaded with a sample, any captured analyte may be detected indirectly by way of a suitable reader. The present invention provides such a reader and an important aspect of the present invention is that no buffer or additional fluid is required other than application of sample to the cartridge. One advantage of this is that the cartridges themselves may be initially "dry", that is contain little or no fluid within the cartridge prior to sample application. This not only simplifies manufacturing of the cartridges themselves, but also improves shelf-life and allows many of the cartridges of the present invention to be stored at room temperature, with little degradation of the chemical or biological components within the cartridge prior to use.

In a further aspect there is provided a method of conducting an assay on a sample, the method comprising:
  introducing a sample into a microfluidic cartridge of the present invention such that any analyte present in the sample is capable of being bound by a binding agent; and
  detecting a level of label (both bound and unbound to analyte), in order to obtain a first reference/control value;
  removing bound analyte from the detection area; and
  detecting any unbound or unreacted analyte that remains after binding of analyte present in the cartridge, or detecting a label which is capable of binding the unbound or unreacted analyte.

Typically, the analyte/binding agent complex and analyte/binding agent/label complex is capable of being removed or transported to another location in the cartridge, in order that the unbound and/or unreacted analyte or unbound label may be detected.

In a further aspect there is provided an assay system for conducting an assay on a fluid sample, the assay system comprising:
  a) a microfluidic cartridge according to the first aspect and comprising paramagnetic particles (or preferred embodiments thereof); and
  b) a reader device, the reader device comprising:
    i) a receiving port for introducing the cartridge into the reader;
    ii) a magnet or magnetic force generating means, capable of applying a magnetic force to the cartridge, so as to be able to remove the paramagnetic particles from the detection area within the cartridge; and
    iii) detection means for detecting any label present within the detection area of the cartridge both before and following removal of an analyte/binding agent complex from a detection area of the cartridge.

Unlike other systems, the present invention is based on the removal of specifically bound complex from the detection area. A first signal may be detected following reconstitution of the label and/or binding agent. The label may be present in excess, so its initial signal is at a maximum or near maximum level. However, upon complex formation and removal of a label/analyte/binding agent complex, from the detection area, such as by application of a magnetic force (if, for example, functionalised paramagnetic particles are used as a capture phase), a decrease in the signal may be detected which is inversely proportional to the amount of analyte present in the sample and hence which was capable of binding to the label and binding agent.

The reader includes a receiving port into which the cartridge is to be inserted. The reader may be adapted so as to ensure correct insertion of the cartridge and this could take a variety of forms. For example, the cartridge may be initially located on a carrier mechanism which enters the reader, such as may be found in computers for loading CDs and the like. Alternatively the receiving port may be sized to allow the cartridge to be received and an internal stop member may be found within the reader which the cartridge abuts once inserted correctly. Additionally, or alternatively, features found on or cut into the surface of the cartridge may be designed to co-locate with features found within the reader and only once the cartridge is correctly located in the reader, will the cartridge be able to be read.

In a further aspect the cartridge is preloaded into the reader, and may be locked in place, forming a combined single-use cartridge and reader. In this aspect the meter and cartridge are not separable and therefore the meter and cartridge can be used once only as a single integrated disposable device.

In the embodiment where the binding agent is bound to the surface of magnetic agents, such as paramagnetic beads, it is understood that the reader will comprise a permanent magnet or electromagnet which is designed to apply a magnetic field or be brought into close proximity or a magnetic field applied, in order to hold the paramagnetic particles in a particular area of said microfluidic channel of the cartridge. This area may be specially located away from the detection area. Concentrating the paramagnetic particles into a particular area outwith the detection area may serve to facilitate detection of any analyte by measurement of unbound label or unbound analyte and/or increase sensitivity of detection. The permanent or electromagnetic field may be reduced or increased, such as by moving a permanent magnet closer to, or further away from the cartridge, or by increasing or decreasing the intensity of the applied field.

In use the magnet or magnetic field may be used to pull paramagnetic particles away from the detection area.

In one embodiment, paramagnetic particles are used to capture analyte and a label used for detection. After a period of time to allow formation of paramagnetic particle-analyte-label complexes to form, a magnet, or magnetic field may be used to pull the paramagnetic particles (including paramagnetic particles complexed to analyte and label) away from the detection area allowing measurement of analyte concentration by the decreasing concentration of label as analyte concentration increases. In this embodiment, the remaining label that is detected in the detection area is any label that is not part of a fully formed reaction complex (that is, is not bound to a paramagnetic particle). This could be unbound free label or label bound to analyte.

The label used for detecting analyte is deposited in such a way so that upon rehydration by cartridge filling by application of sample the label (and other reaction components) is distributed throughout the the detection area. The initial signal generated by the label is therefore independent of analyte concentration, and can form an important baseline for the specific measurement which is made after removal of label that has been bound to the capture phase reagents (such as functionalised magnetic particles) via specific analyte binding.

The reader of the present invention further comprises detection means for detecting any captured analyte within the sample cartridge. The detection means may be any suitable means depending on the particular assay. For example, the detection means may be a potentiostat, which may be used to detect an electrochemical signal, once generated by the labelled or unlabelled bound analyte or reaction product. The bound analyte/reaction product may have intrinsic electrochemical properties and may be measured, for example, by current generated after an appropriate potential has been applied, or a further label may be used to separately bind the bound analyte and the label detected by electrochemical means. Other labels which may be employed and hence the detection means adapted accordingly, include fluorescent labels, radiolabels, phosphorescent labels, colloidal metal particles, bioluminescent labels, colourimetric labels and the like. Moreover, as mentioned above the bound analyte or radiation product itself may be directly detected using techniques such as Raman spectroscopy and the like. Also, measurements of absorbance of naturally occurring components of the sample, or species generated by a chemical or enzymatic reaction or label could be used.

When the reader uses electrochemical detection the methods of signal measurement include, but are not limited to chronoamperometric, potentiometric, impedance, linear sweep, charge transfer, potentiometric stripping, galvanometric, voltametric analysis (differential pulse, square wave, sample DC, normal pulse, AC voltammetry, AC second harmonic, differential normal pulse) and the like.

The detectable labels may be used alone, or in conjunction with a microparticle or bead, such as a metal oxide, polysaccharide or latex particle. Many types of latex and other particles are known in the art The reader may include other features, such as a heating device to allow assays to be conducted at a particular temperature, as well as appropriate electrical circuitry and software to allow the reader to be programmed to carry out one or more different assays.

The platform system of the present invention, comprising cartridge and reader provides a number of distinct advantages:

1. Reduced Sample Volume: capillary introduction of a fluid, such as a finger stick blood sample, reduces the complexity for the user and allows the tests to be performed in any environment (e.g. ambulance, point of care, doctor's surgery, battle field, home etc), and similar to glucose testing, allowing products to be placed anywhere.
2. Room Temperature Stability: Many existing IVD tests require refrigerated storage and shipping, this requirement adds significant cost to the product and also restricts the usage and distribution of the product. The initial "dry" nature of the sample cartridges aids in their stability and shelf-life. In addition, the specific assay method described in this patent allows for an initial background measurement before the removal of specifically bound complex from the detection area. This initial background measurement can be used for correction purposes.
3. Low material costs and a simple manufacturing process allow for low costs of goods (COGs), allowing substantial and increased profits to be generated by the sales of IVD strips. This is especially needed in the immunoassay and molecular IVD market where the conventional tests tend to be of high complexity driving both the strip material costs and overall assay cost higher.
4. Low cost of reader. No need for a wash buffer which simplifies reader mechanics. Use of simple detection methods such as, electrochemical or simple optical measurements, allows the reader instrumentation to be kept simple and therefore at low cost also.

DETAILED DESCRIPTION OF THE INVENTION

The present invention will now be further described by way of example and with reference to the figures which show:

FIG. 21 shows a table of the difference between post magnetic separation current and the pre magnetic separation current for all concentrations of PSA in accordance with the current invention;

FIG. 23 shows a table of the ratio of the post magnetic separation current to the pre magnetic separation current in accordance with the current invention;

Figure 1:
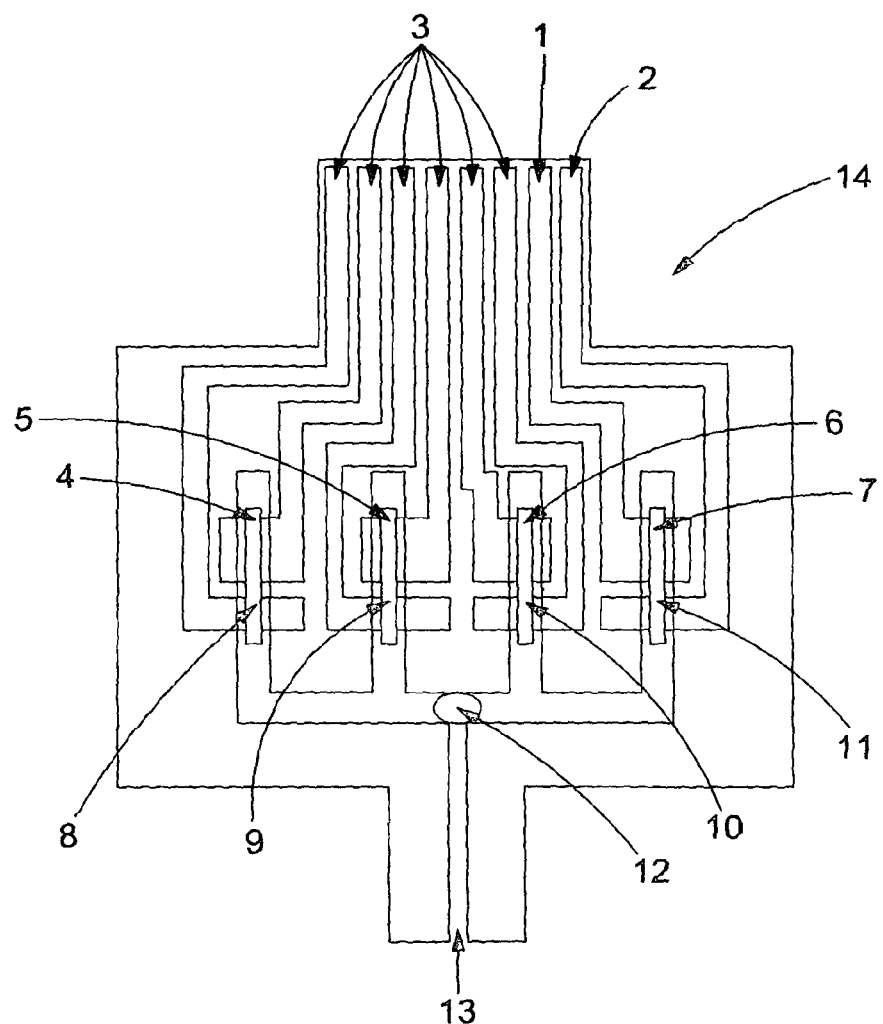
FIG. 1 shows a schematic representation of a sample cartridge in accordance with the present invention.

A sample cartridge (14) in accordance with an embodiment of the present invention is shown in FIG. 1. A fluid such as blood is applied to the sample introduction port (13) (via, for example, finger or venous blood). In this particular embodiment four channels (4,5,6,7) span from this one sample introduction port (13). Although not to be construed as limiting, the further description will relate to the sample being a sample of whole blood.

Figure 12:
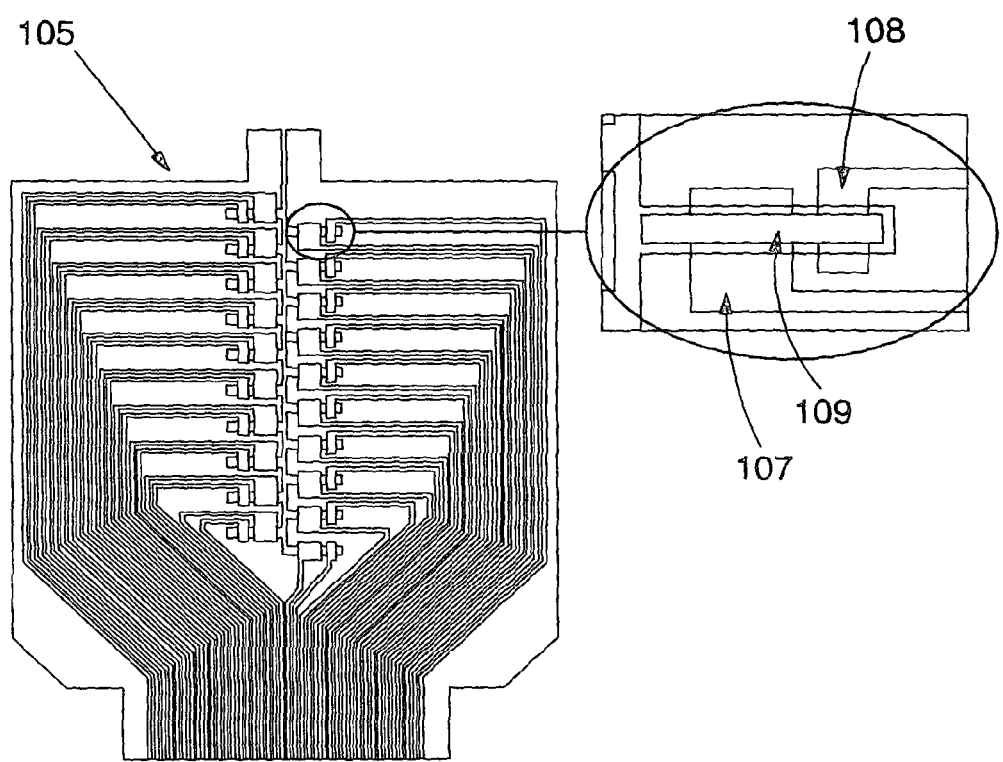
FIG. 12 shows a schematic of the disposable cartridge including 20 measurement channels in accordance with the present invention.

The blood is applied to the sample application port (13), the initial single channel splits into 4 separate channels. Each channel allows a measurement to be made, this could be 4 measurements of the same analyte resulting in replicate results of a single analyte or a different analyte could be measured in each channel. A 4 channel version of the strip is shown in FIG. 1. A 20 channel strip (105) is shown in FIG. 12, with a photograph of a physical embodiment (106) of the strip with 15 channels shown in FIG. 13. In FIG. 12 a close up of the electrode configuration shows a counter electrode (107), a working electrode (108) and relevant reagents (109) deposited homogenously, such that the detection zone (108) is located within the area of the channel where the analyte binding by specific reagents occurs. An alternative embodiment in FIG. 14 shows a strip design (110) where a common counter electrode (111) is utilized as opposed to having a separate counter electrode for each working electrode. This common counter electrode allows the electronics in the reader to be simplified and also allows the disposable cartridge size to be reduced as the disposable cartridge width is influenced by the total number of electrodes. With a separate counter electrode for each working electrode, the total number of electrodes is 40 for a cartridge capable of 20 working electrode measurements, while for a cartridge with a common counter electrode, the total number of electrodes is reduced to 21.

The total sample application may be as small as less than 1□l depending on the number of channels to fill therefore when the user applies a sample, such as a drop of blood, all channels (4,5,6,7) will fill under capillary force. This process is very fast and more in tune with blood glucose strip filling as opposed to the lengthy blood separation filling of some immunoassay platforms. Deposited in the four channels (4,5,6,7) are paramagnetic particles functionalised with antibody and label functionalized with antibody and label enzyme, as well as anti-heterophile reagents, stabilising agents, electrochemical mediator and anticoagulant (8,9,10, 11). Deposited in the sample introduction port (12) is enzyme substrate which is converted to an electrochemically measurable species by the label enzyme (13) to produce a measurable signal for detection by the reader.

The electrodes present in each channel (1,2,3) are used to make the electrochemical measurements, however in other examples optical or other methods of detection measurements could be made. The electrodes are also used to tell the user when enough blood has been applied to the cartridge.

Figure 2:
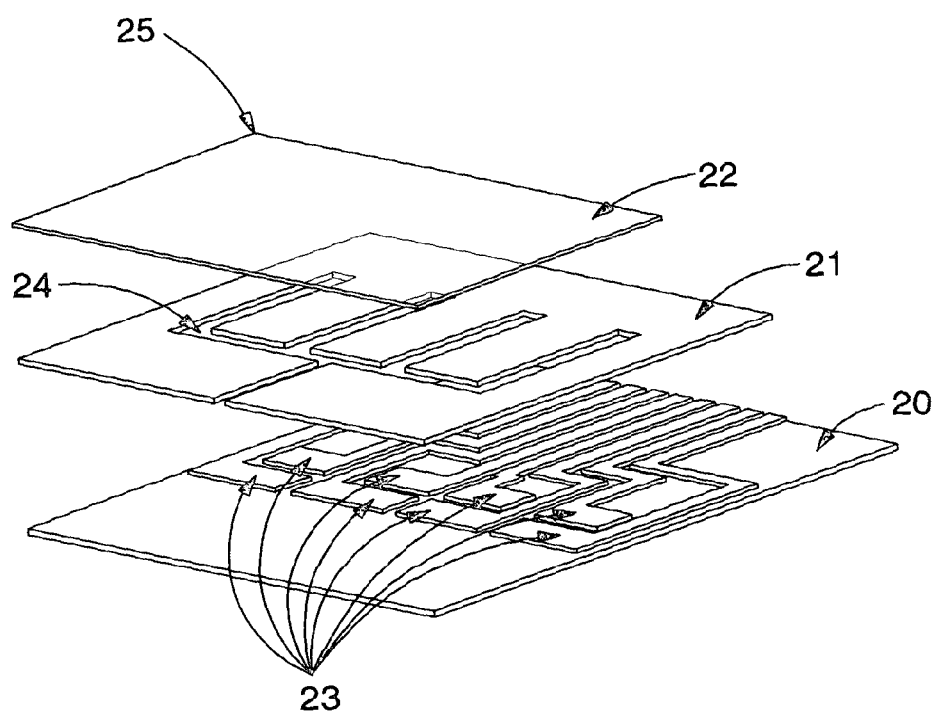
FIG. 2 is a schematic representation of how a cartridge of the present invention may be formed.
Figure 15:
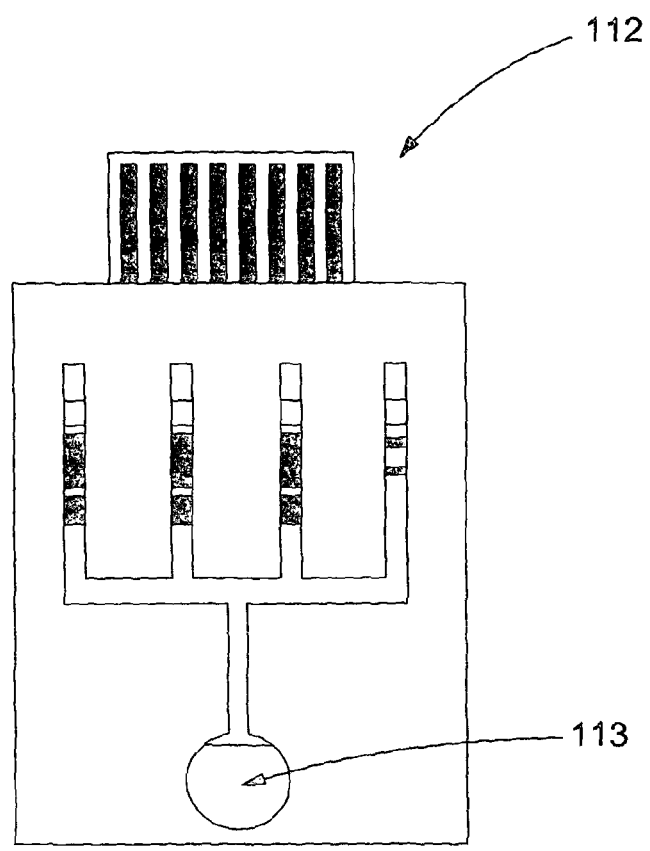
FIG. 15 shows a photograph of a physical embodiment of a disposable cartridge including 4 measurement channels in accordance with the present invention.

When the cartridge (14) is formed from three substrates (20,21 and 22) as shown in FIG. 2 the channels are formed by removal of material from an adhesive layer (24), sandwiched between a base layer (20) with screen printed electrodes (23) and a lid layer (22). In FIG. 2, the lid (22) is shorter than the channel formed in the adhesive (24) which forms an air vent where the edge of the lid (25) meets the channel (24), when the cartridge is assembled. This allows the cartridge to fill by capillary force, and also forms a fluidic stop feature. FIG. 15 shows a photograph of a physical embodiment of this strip design (112). In this particular embodiment there is a circular aperature (113) cut in the top lid to allow the filling of the device by applying a drop of sufficient volume of sample into this circular area.

As the cartridge (14) is inserted into the reader, a cartridge heating mechanism may be initiated, heating the cartridge to a predefined constant temperature for the duration of the test.

In each of the four sample channels (4,5,6,7) on the cartridge there may be electrodes (1,2,3 in FIG. 1). Through the reader, checking the electrical continuity between the electrodes, the reader will be able to confirm that the channels (4,5,6,7) have been successfully filled with sample. This can be performed through a simple conductance measurement. For a specific channel, if the electrodes (1,2) have been successfully wetted with blood (meaning that the channel (4) has been filled completely with sample) then an electrical current can conduct from one electrode to the other through the blood sample. Otherwise if the blood sample is not present, or has only partially filled the channel, then at least one of the electrodes will not be wetted, meaning the electrical current cannot flow from one electrode to another. Additional electrodes can be added to each channel for more accurate determination of device filling (to ensure sample has completely covered the electrodes used in analyte detection). An additional electrode positioned downstream (in relation to the flow of sample upon addition to the cartridge) of the other electrodes in each channel would satisfy this. The current flow between these additional electrodes in different channels would then indicate that those channels were both full, or lack or current flow would indicate that one or both channels were not full of sample.

In the present cartridge/assay system, it shall be possible to measure the hematocrit of the blood sample.

Figure 3:
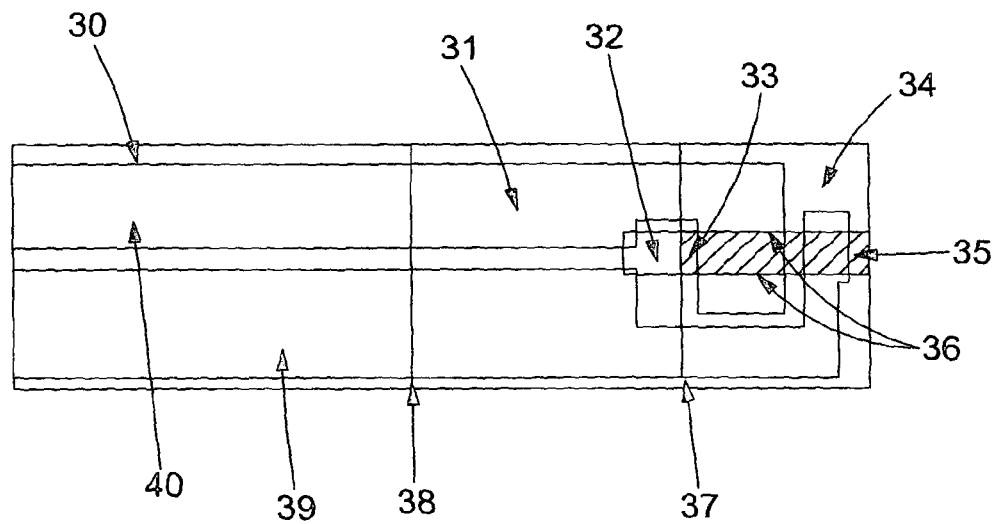
FIGS. 3 and 4 are photographs of a cartridge according to the present invention showing various features.

FIG. 3 shows a photo of a single channeled cartridge (41) with the channel filled with fluid (33) up to the end of the channel which has been defined by the edge of the lid (37) producing an air vent (32) which allows the device to fill by capillary force and forms a fluid stop feature.

Figure 4:
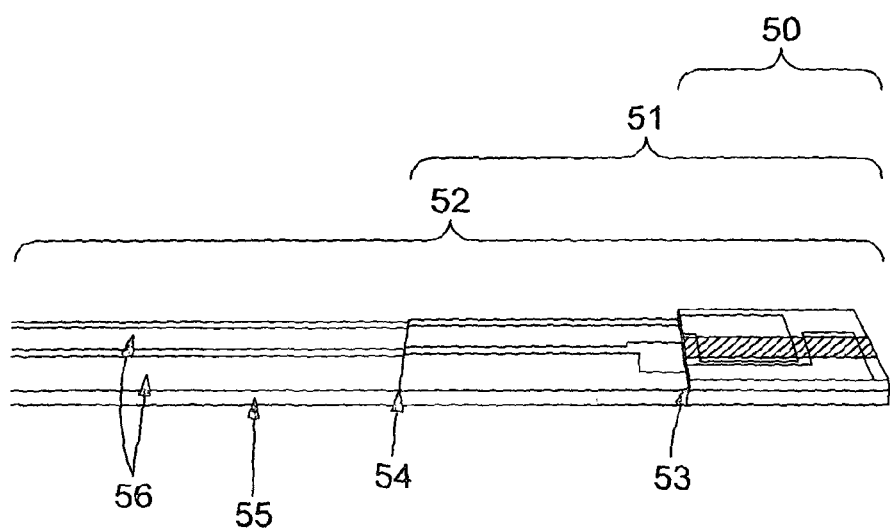

The inner surfaces of the channel are required to have some hydrophilic properties to allow filling by capillary force. In one embodiment two hydrophilic surfaces are utilised however alternative combinations of hydrophilic/hydrophobic surfaces could be used to fill the strip by capillary action In FIG. 3 the sample has been applied to the sample introduction port (33) and fills the channel formed by the adhesive layer (31), with channel edges indicated (36), between the base layer (30) with printed electrodes (39,40) and the lid layer (34). The electrodes are left exposed (39, 40) as the adhesive layer stops before the end of the device (38), as does the lid layer (37). This allows the electrodes to be connected to the reader. This can be seen more clearly in FIG. 4 which shows an angled side view photograph of the same single channel device as depicted in FIG. 3. In FIG. 4, the base layer (52) with printed electrodes (56) is partially covered by an adhesive layer (51) where the edge can be clearly seen (54). The adhesive layer (51) is partially covered by a lid layer (50), where again the edge is visible (53).

As the blood fills the sample channel (33) (see FIG. 3) the pre-deposited dried reagents are resuspended by the blood, thereby allowing binding any analyte/s present. Potential positioning of dried reagents are shown in FIG. 1 (8,9,10, 11,12). The blood fills the channel (33) to the stop features (37), see FIG. 3. Once the functionalised capture and detection reagents are resuspended, incubation with the blood sample would be allowed to occur for a defined period of time (incubation time) and controlled by appropriate software and programming of the reader. Paramagnetic particles may be chosen as the capture phase and particles (eg latex) or conjugates chosen as the label, or detection phase due to their high mobility and functionality (size dependent i.e. diffusion coefficients etc) to reduce diffusion distances and ultimately incubation time. This type of reaction will be very efficient and reproducible at binding analyte from blood samples. During the capture and detection phase binding of analyte, a hematocrit measurement may performed by electrodes (39,40). The hematocrit value can be used by the reader to calculate the final concentration of the analyte as the reference value may be a plasma measurement made by a clinical analyser. A hematocrit measurement may be required to correct for the concentration difference associated with analyte present in a given volume of sample due to differing ratios of red blood cells to plasma. Therefore a whole blood measurement may be corrected for this difference by means of a hematocrit measurement so that results are consistent with those associated with a plasma sample.

After the capture phase and detection phase reagents have bound any analyte in the blood a permanent magnet or electromagnetic field can be used to remove the paramagnetic particles (including paramagnetic particle-analyte-label complexes) from the vicinity of the working electrode (In FIGS. 3, 39 and 40 represent the counter/reference electrode and working electrode where either electrode could be configured through the reader for either function). In this case, detection of the remaining label (either directly or through a label-catalysed or label-mediated reaction) can then be detected by electrochemical means at the working electrode.

Figure 13:
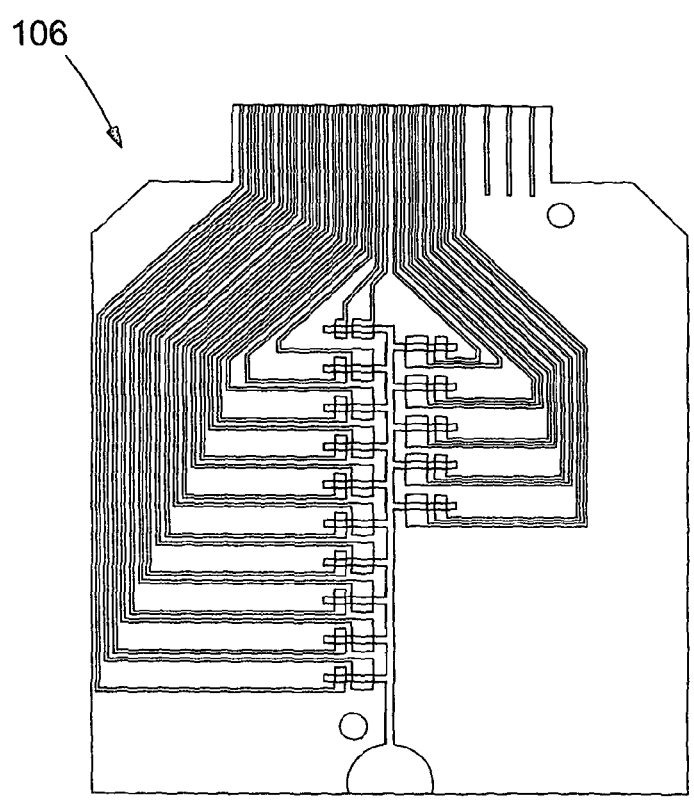
FIG. 13 shows a photograph of a physical embodiment of a disposable cartridge including 20 measurement channels in accordance with the present invention.
Figure 14:
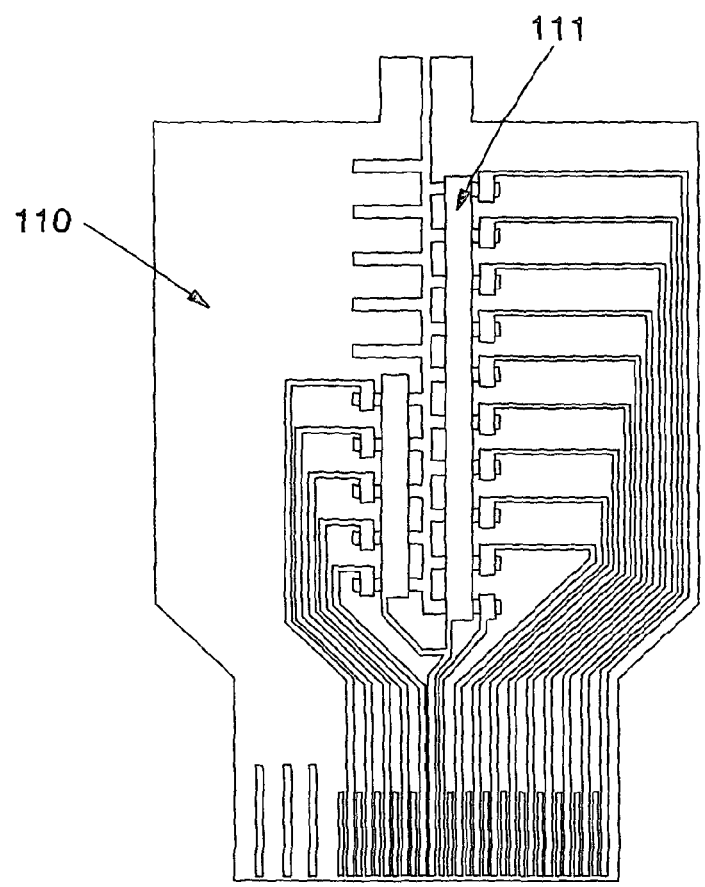
FIG. 14 shows a schematic of a disposable cartridge including a single common counter electrode in accordance with the present invention.

It should be appreciated that the foregoing description, with reference to FIG. 1, has been made in relation to a four channel cartridge, and in relation to FIGS. 3 and 4 a single channel cartridge, but the present invention also relates to multi-channel e.g. 6, 7, 8 etc cartridges, with an example of a 20-channel cartridge shown in FIGS. 12, 13 and 14. Each channel may carry out the same reaction for reproducibility/accuracy purposes, or may be designed to carry out different assays—in this way each cartridge may be capable of carrying out a "multi-plex" reaction.

Figure 5:
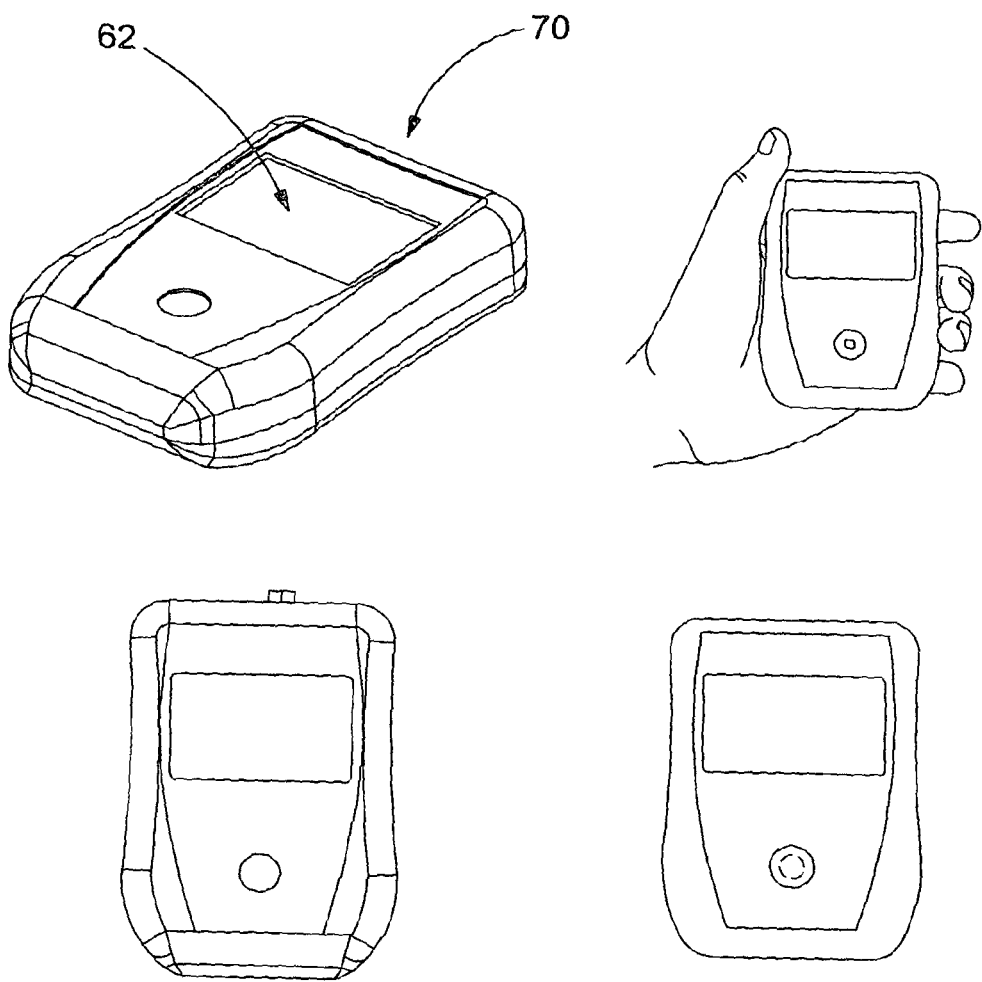
FIG. 5 is a schematic and schematic view of a reader device in accordance with the present invention.
Figure 6:
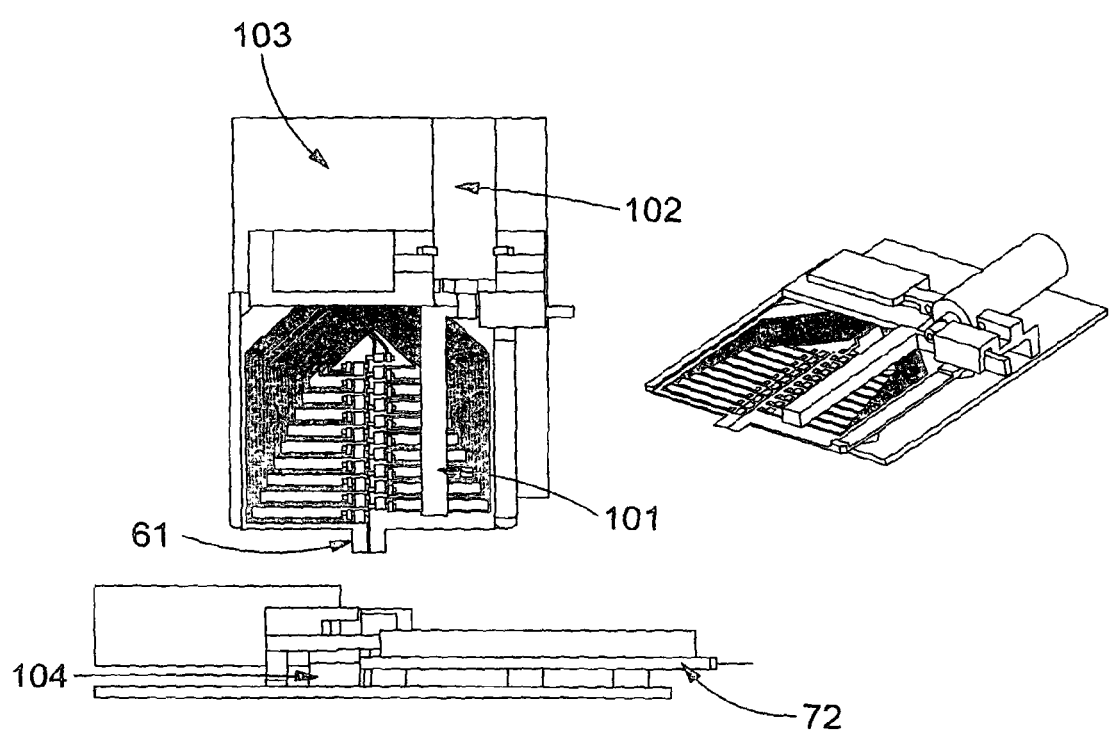
FIG. 6 shows a schematic representation of the reader internal mechanisms.

Ultimately a measurement is made (e.g. electrochemical) by a reader using electrical, optical or other detection means, suitable for the label to be detected. For example, if the label is an enzyme which catalyses a reaction which generates a product that is electrochemically active, the detection means may be electrical, via electrodes within the cartridge, see FIG. 3 (39,40). Schematic views of a hand held reader in accordance with the present invention are shown in FIGS. 5 and 6. The reader (70) comprises a platform (72) for receiving and holding a cartridge (61) of the present invention. There is also provided suitable detection means; a PCB (103) comprising a connector to interface with the cartridge (104), electrical circuitry and an associated computer chip or chip(s) and software for controlling the reader and conducting the assay. In addition because the described system has the flexibility to perform assays using paramagnetic particles, the meter has the functionality to move a permanent magnet (101) via a motor (102) in the proximity of the cartridge. For example, towards the cartridge and away from the cartridge, or in any other orientation in order to manipulate the paramagnetic particles as required.

The reader can also control the temperature of the sample applied to the cartridge by means of active heating in the case where the cartridge platform (72) comprises of a material that is conducive to conducting heat FIG. 5 shows envisaged physical embodiments of the meter where a result can be displayed on the reader screen (62).

Figure 9:
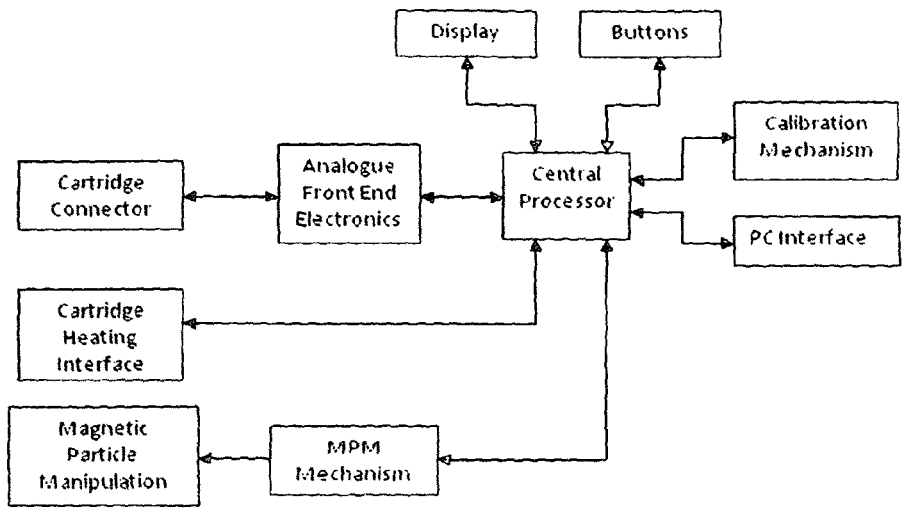
FIG. 9 shows the instrument functionality block diagram in accordance with the present invention.

The primary functions of the reader are described in FIG. 9, the reader functionality block diagram, and are as follows:
1. Cartridge Signal Measurement
2. Cartridge Temperature Control
3. Paramagnetic Particle Manipulation
4. Calibration Mechanism Cartridge Signal measurement: The reader shall be capable of exposing each of the separate test channels to separate precise electrical signals in order to commence, maintain and control the required electrochemical reaction that is to be conducted within the particular test channel of the test cartridge. Examples of such electrical signals are steps from one voltage potential or from an open circuit state to another voltage potential state, a linear sweep from one potential to another in a defined time, or the creation of a non linear waveform for example a sine wave of a particular frequency and voltage magnitude. The reader may use analogue switching multiplexers in order to switch between different measurement channels.

The Instrument shall be capable of measuring the electrical/electrochemical response from each test channel separately. Examples of the signals to be measured from the test cartridge are direct or alternating currents or a voltage potential. The reader may use analogue switching multiplexers in order to switch between different measurement channels.

The reader shall have a connector that makes physical contact with the printed electrodes on the test cartridge to ensure the delivery of electrical signals to and from the cartridge. This connector could be mounted directly on to the PCB of the reader.

As the proposed system comprises of a cartridge and reader with the ability to perform multiple measurements, for example 20 separate measurements on a single applied test sample, the system is capable of using these multiple measurements to produce improved results with regards to accuracy and reliability.In the instance where the test system is used to measure multiple separate measurements of the same analyte, the system would be able to perform a mean or truncated mean analysis of the obtained 20 results. For truncated mean analysis, this would involve the instrument software sorting the 20 results in order of magnitude, removing a number of the highest and lowest results (e.g. 5) and taking an average of the remaining (e.g. 10) results. The benefit of the truncated mean over a standard mean is that results that are statistical (or practical) outliers can be removed from the data set before the mean is taken. This removes the risk of abnormal results shifting the resultant mean substantially higher or lower than the expected result.

In the case of a low cost assay system the specific improvements associated with this methodology include the ability to remove results that are abnormally high or low due to factors such as incorrect test sample volume, incorrect reagent deposition volume, incorrect reagent formulation, and physical or environmental damage to the test sample channel or associated reagents. The system discussed in this patent is particularly suited to this truncated mean analysis as each of the sample channels in the test cartridge are truly separate including a separate reagent deposition, a separate detection means (e.g a working and counter electrode) and a separate sample channel.

The system could be configured to measure multiple measurements of multiple analytes and therefore improve the accuracy of the results for multiple analytes within a single test.

Cartridge Temperature Control: The reader shall be capable of controlling the temperature of the test cartridge. The mechanical design of the reader shall result in the instrument PCB being in contact with the test cartridge. Therefore it would be possible to have the heat generated from a source (for example a high wattage low value resistor, a MOSFET transistor or a thin film flexible printed circuit board heating element) coupled into the cartridge through the instrument PCB. This could be achieved by having a bared copper area of the PCB in contact with both the test cartridge at one point, and the heat source at another point.

Alternatively the reader design could comprise of a separate heating block made of suitable material for heat transfer to the test cartridge, such as aluminium. This separate heating block could be place within the reader such that it is in direct contact with the test cartridge.

The control of the heating of the test cartridge shall come by placing one or more temperature sensors in contact with the surface that is in direct contact with the test cartridge. The reader can then monitor the temperature that the test cartridge is being exposed to and adjust the amount of heat energy being transferred to the cartridge accordingly through controlling the heat source. (For example decreasing or increasing the amount of current flow through a MOSFET).

Paramagnetic Particle Manipulation: The reader shall be capable of gathering the paramagnetic particles contained within the test channels of the test cartridge to a pre defined position. For example, the reader may gather the paramagnetic particles on the cartridge surface opposite the test channel working electrode, or it may gather the paramagnetic particles to another location on the test channel specially separated from the detection area. One method of achieving this would be to use a permanent neodymium magnet to gather the paramagnetic particles. A mechanism could be implemented where the magnet can be physically moved in a single plane such that at one point in the mechanism movement it is in physical contact with the cartridge, meaning that the paramagnetic particles are gathered by the magnet, and at another point there is a physical distance between the magnet and the test cartridge, meaning that the paramagnetic particles are not under the influence of the magnetic field associated with the magnet.

The physical movement of the magnet in one plane could be motorised through the use of, for example, a linear actuator, or through a rotational motor using a gearing system, or through a clockwork mechanism, or through a mechanically sprung mechanism, or through a manual mechanism whereby the movement of the magnet is initiated and controlled by the user of the instrument.

In a different embodiment, the permanent magnet could be replaced by an electromagnet, in which case the control of the paramagnetic particles could be performed by energising or de-energising the electromagnet. Alternatively the reader could implement a stationary permanent magnet in a fixed position where the paramagnetic beads are to be gathered.

Using these different methodologies, the reader could affect the paramagnetic beads in such a way as to collect them to a particular location associated with the cartridge from their previously scattered state. This location could result in the paramagnetic beads being moved from one surface of the cartridge to another or along a surface of the cartridge, or between the cartridge surfaces or a combination of any of these.

Calibration Mechanism: Due to the variation in processes associated with the manufacturing of disposable assay test cartridges it is normally required for each batch of cartridges to be characterised and for specific calibration values to be entered into the reader so that the assay response generated by the test cartridge can be normalised by the reader internally before the final assay result is reported. In order to overcome this issue the reader could have different sets of calibration parameters pre loaded into its memory. The reader would know what set of calibration parameters to use for a particular test cartridge due to the value of a surface mount resistor that could be mounted either on the test strip itself or on a separate substrate that can be inserted into the meter independently of the test strip and in a different location. The instrument could then measure the value of the surface mount resistor which would be related to a specific set of pre loaded calibration parameters. Set bands of resistances could relate to set calibration codes. Alternatively the resistor could be replaced with a capacitor, and the reader could attribute different levels of capacitance with a calibration code. Alternatively, the resistor could be replaced with an inductor, and the reader could attribute different levels of inductance with a calibration code. Alternatively, a combination of any resistors capacitors and inductors could be used.

It is a physical feature of assay development that the ambient temperature can influence the magnitude of response. In the present invention, this temperature effect will be driven through the effect of temperature on diffusion, whereby an increase in temperature can result in increased binding efficiency between the paramagnetic beads and the target analyte, and the label and target analyte. Temperature effects on enzyme activity will also make a significant contribution to the assay response where enzymes are used. The present system may be used, for example in a doctor's office and home use, and the range of temperatures the system may be exposed to will be broad, from perhaps as low as 10 degrees Celsius to as high as 40 degrees Celsius. One method of removing this temperature effect is in the heating of the test strip to a pre determined temperature, for example 40 degrees C. This would remove any variation associated with the assay due to temperature effects. Heating the cartridge also helps to minimise any blood to blood effects due to differences in viscosity. Thus, the reader may also comprise temperature control means, such as a heater as previously described.

In one particular embodiment, the sample cartridge and associated reader are designed for carrying out an immunoassay, where the analyte to be detected is an antigen and the binding agent is an antibody. Paramagnetic particles may be functionalised by attachment of antibodies against either free or free and complexed antigen.

Although not to be construed as limiting, the further description will relate to the sample being a sample of whole blood and label detection being enzyme driven electrochemical detection, and a paramagnetic particle capture phase.

As the blood fills the sample channels of the cartridge, the reagents which are pre deposited in the initial channel (12) see FIG. 1, and within each of the channels (8,9,10,11) as dry reagents, are resuspended by the blood and start binding the analyte/s. The deposited reagents within each channel (8,9, 10,11) contain paramagnetic particles functionalised with an anti-analyte antibody, a label (e.g. an anti-analyte antibody-enzyme conjugate), electrochemical mediator, anti-coagulant, anti-heterophile reagents and stabilisation reagents. In comparison the reagents deposited in the initial feed channel (12) contain the enzymatic substrate.

As the blood fills the strip the dried enzymatic substrate is resuspended and is transported by the blood into the 4 measurement channels (where the enzyme substrate is in excess). The other reagents in each channel are resuspended as the blood fills each channel. The anti-analyte antibody-enzyme conjugate immediately starts converting substrate and reacting with the electrochemical mediator. The electrochemical mediator is converted from the reduced form to the oxidised form. At the same time the analyte is being bound by the immunoassay binding reagents (paramagnetic particles functionalised with an anti-analyte antibody and an anti-analyte antibody-enzyme conjugate (label)). These homogenous events which are occurring throughout the channels are allowed to occur for a defined period of time (binding time, such as 2-4 minutes). These processes and the following processes are occurring in all 4 channels, it could be for the same analyte or for a different analyte in each channel whereby the antibody pairing would be changed.

An electrochemical measurement is initiated at a defined time; this could be at the end of the binding time, during the binding time or immediately as the strip is filled. A chronoamperometric measurement is made whereby the current is measured at the electrochemical reduction potential of the mediator (the electrochemical mediator is being converted to oxidised form by the label (free and bound)). At this point all concentrations of analyte will have the same rate (current per sec) calculated from the chronoamperometric transient.

After the defined binding time a magnet (permanent or electromagnet) is applied to the lid surface opposite the electrodes surfaces. The paramagnetic particles are pulled via magnetic attraction to the inner lid surface. The working electrode is only measuring the sample immediately above it, therefore when the paramagnetic particles are magnetically pulled to the inner lid surface opposite the electrodes they will contain a mixed paramagnetic particle population. The paramagnetic particle population will be split between paramagnetic particles with no analyte bound, paramagnetic particles bound to analyte, and paramagnetic particles bound to analyte and label (fully formed sandwich immunoassay complex).

The number of sandwich immunoassay complexes formed will be proportional to the concentration of analyte in the blood sample. The higher the analyte concentration in the blood the more immunoassay complexes formed and hence removed from the vicinity of the working electrode during the magnetic accumulation. This process is therefore changing the enzyme label concentration at the working electrode and is occurring in an analyte concentration dependant manner. This process is measured in real time; therefore the rate calculated from the chronoamperometric transient is proportional to the enzyme concentration which is proportional to the analtye concentration. The rate therefore decreases as the analyte concentration increases (the more enzyme bound the more immunoassay complexes are formed). The assay format is therefore not a conventional heterogenous assay format but more in tune with a homogenous assay format. This assay format is summarised in FIG. 10, specifically for an enzyme label using electrochemical detection.

Figure 10:
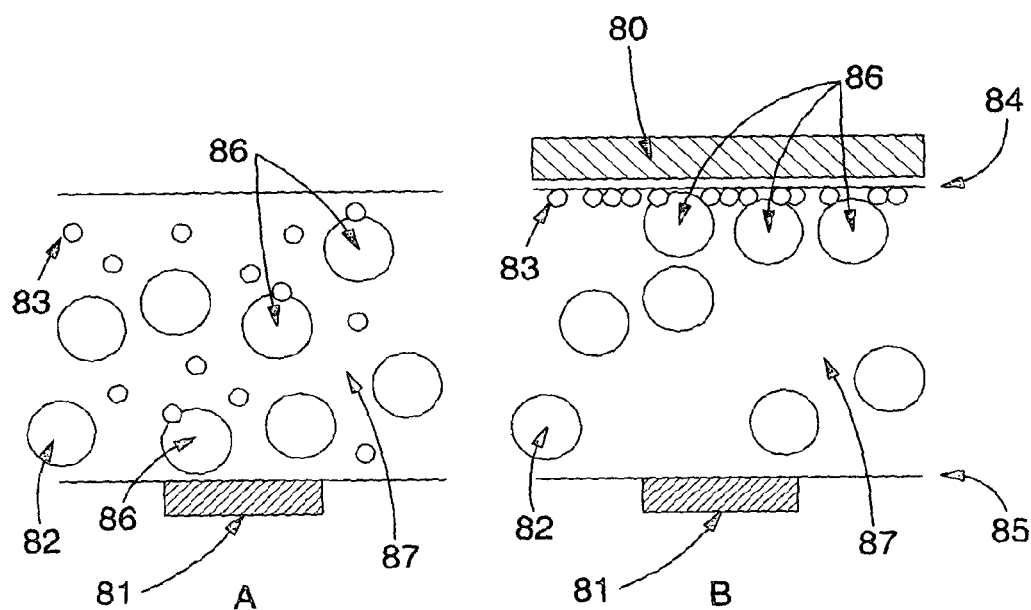
FIG. 10 shows a schematic representation of an example homogeneous immunoassay format in accordance with the present invention.

FIG. 10 is a schematic of the homogeneous immunoassay format, with each image (A and B) representing schematically a cross section through the channel in a cartridge, with the channel top (84) and bottom (85) indicated and shows the working electrode (81) before (FIG. 10A) and after (FIG. 106) the presence of the magnetic field. In A, label particles (82) and paramagnetic particles (83) are rehydrated by sample (87). The sample has also rehydrated enzyme substrate and electrochemical mediator so the enzyme label is reacting with this substrate and mediator from the onset of rehydration. In A the binding reaction is also occurring between the magnetic particles, analyte and label with fully formed immune complexes shown (86). Although only the area above and around the working electrode is shown, this process is occurring throughout the whole channel. The electrochemical measurement would begin in A, after a defined period of binding time; the magnet (80) is applied to the top surface (84) opposite the electrode surface (84) as shown in B. All of the paramagnetic particles are accumulated irrespective if an immune complex is formed or not. The amount of enzyme label accumulated with the paramagnetic particles is dependant the on the number of immune complexes formed which is proportional to the analyte concentration. Because the paramagnetic particles and all fully formed immune complexes are removed from the vicinity of the working electrode by the application of a magnet, as the analyte concentration increases, the electrochemically measured rate/response decreases. Although in this example the magnetic force is applied to the surface opposing the working electrode, the magnetic force could be applied anywhere in the sample channel whereby paramagnetic particles are removed from the detection zone.

In a desired embodiment of the present invention, the paramagnetic particle and label are used to form an immunoassay sandwich by capturing the analyte, with the capture and label antibodies recognizing different antigen epitopes. The desired embodiment of the current invention assay format is to use glucose oxidase (GOD) as the label enzyme. GOD has been extensively used for the measurement of blood glucose. Specifically an excess of GOD and electrochemical mediator is dried in a strip, the GOD reacts with the glucose contained in the blood, converting an electrochemical mediator from the oxidised to reduced form which is then electrochemically measured at a electrode. This system works well as alt the reaction components are in excess so the glucose concentration is the rate determining factor. GOD has been used as enzyme label for ELISA measurements however in electrochemical immunoassays GOD has been found to be fairly insensitive as an enzyme label. This is driven from the fact that directly coupled electrochemical mediators have been employed. Oxygen is the true acceptor for the GOD reaction, but ferricyanide is used as an artificial acceptor to electrochemically couple the reaction so an electrochemical measurement can be performed. This reaction between ferricyanide and GOD is very unfavourable compared to oxygen and is overcome by very high ferricyanide concentrations. This problem is also overcome in glucose sensors as GOD itself is in excess therefore any inefficiency becomes insignificant. In an enzyme based immunoassay the enzyme concentration is measured, therefore unfavourable interactions between GOD and ferricyanide results in a sensitivity problem. The desired embodiment of the present invention overcomes this problem by using a further coupled reaction as summarised in FIG. 11: The GOD coverts glucose and oxygen into gluconolactone and hydrogen peroxide respectively (using FAD as the cofactor of GOD). Horseradish peroxidase (HRP) and ferrocyanide are present in large excess (as is glucose), therefore any hydrogen peroxide produced will be immediately used by HRP to convert ferrocyanide to ferricyanide which is then measured at the electrode with an electrochemical reduction reaction (this then electrochemically reduces the ferricyanide back to ferrocyanide with the loss of electrons from the electrode). The GOD becomes much more sensitive as an enzyme label as it is no longer forced to artificially react with ferricyanide, and its turnover of glucose is unhindered therefore lower GOD concentrations can be measured. This is true of all enzyme labels; the enzyme rate for the natural reaction is greater than any conceived coupled system whereby a measured event has been forced into the enzyme reaction. Using an enzyme cascade allows this problem to be avoided as in the secondary reaction both the enzyme and the mediator are in excess and not rate limiting.

There are a number of advantageous to using the described scheme:
1. The GOD reaction is unhindered allowing sensitive measurements of GOD concentration.
2. GOD is well known as a robust stable enzyme hence its use in the blood glucose monitoring products. Other labels such as HRP are known not be as stable, HRP instability in this embodiment of the current invention can be overcome by enzyme redundancy (vast excess).
3. An electrochemical reduction is performed to measure the concentration of ferricyanide generated by the GOD/HRP reaction. A reduction reaction will significantly reduce the influence of electrochemical interferents in the blood. Most interferents interfere with oxidation reactions.
4. There are no linearity problems with respect to the electrochemical measurement as all the components are in large excess (due to high solubility) unlike some other HRP and other enzyme substrates (such as alkaline phosphatase) where excess cannot be achieved.
5. In most assays a background measurement is determined by signal magnitude measurements during calibration. This background measurement is an average value, normally with a large associated error. The background can vary significantly due to any variations in reagent concentrations deposited, variations in detection areas, blood to blood differences etc. This decreases the sensitivity of most assays. In this system the background can be measured in each channel before the magnet is applied and the specific signal measurement made. In this way each measurement can be individually background corrected, which allows for very sensitive and accurate assay results.

Due to the ability to have multiple channels within a cartridge, there is a great opportunity to extend analyte measurement ranges. For example, typical immunoassay dose response curves are sigmoidal. This is driven by either reagent saturation (insufficient reagent to maintain linear binding) or saturation of the label/detection method (i.e. the detection methods becomes saturated and can no longer measure the label in a linear fashion). The present platform may however, allow a full linear response across the measurement range if required, and this can be achieved by having different reagents, or reagent concentrations in different channels. For example, the reader can measure the concentration of the label in one channel with reagents designed and manufactured for very high sensitivity, but that have a limited range. Reagents in a second channel could be designed and manufactured to have lower sensitivity but greater range for the same analyte. Therefore, if the signal achieved in the first channel is over a threshold value (ie above the measurable range of that assay set during calibration, representing a high analyte concentration) the signal from the other channel would be used and vice versa, if the signal from the second channel was below its threshold value (ie below its measurable range set during calibration and representing a low analyte concentration) the signal from the first channel would be used to determine analyte concentration. The present platform allows different ways of achieving linear responses across the measurable range, which will allow more accurate calibration resulting in better within and between sample precision resulting in better ATE. If a measurement were made before the paramagnetic particle complexes are removed from the detection area, this gives a background measurement which can be used to normalise the results and therefore correct for any variations that may occur such as label concentrations or exposed detection area etc.

Multiple channels also provides the functionality to combine different tests on the same cartridge where one channel could have reagents designed for measurement of, for example, creatine kinase (CK), and another channel with reagents designed for the measurement of, for example aspartate aminotransferase (AST), and another channel designed for the measurement of, for example hematocrit (Hct). Such a combination of tests has great potential use in the veterinary field for use on blood samples, for example from horses. In the case of these analytes, CK and AST could be measured by a sandwich immunoassay using a scheme such as that described in FIG. 10. Either or both could also be detected using their enzymatic activity producing detectable reaction products through enzyme linked reactions. These tests could be combined on a cartridge with a hematocrit measurement using conductance of blood sample between two electrodes. Different analytes could also be detected within a channel. For example, fluorescent labels with separate emissions could be functionalized against different analytes and used with magnetic particles functionalized against all analytes to be detected in a reader with the detection capability to read the signals produced from all the different label emissions.

Here follows experimental data generated by a specific embodiment of the current invention. The electrochemical detection of signal is made by a commercially available potentiostat, in place of the reader.

Electrochemical Assay of Total PSA (I)

Materials

Neutravidin: Thermo Scientific, Cat 31000 (Neutravidin biotin binding protein).

Maleimide-PEG2-biotin: Thermo Scientific, Cat 21901 (EZ-link maleimide-PEG2-biotin).

Latex particles: Invitrogen, Cat C37259 (CML latex, 4% w/v, 10 um)

Paramagnetic particles: Ademtech, Cat 03223 (200 nm Strep+paramagnetic particles)

Antibody 1H12: Hytest, Cat 4P33 MAb 1H12 (Anti-PSA, human)

Antibody 5A6: Hytest, Cat 4P33 MAb 5A6 (Anti-PSA, human)

bGOD: Rockland, Cat B000-07 (biotinylated glucose oxidase)

PBS: Thermo Scientific, Cat 28372 (BupH phosphate buffered saline packs)

BSA: Sigma, Cat A4503-50G (Albumin, from bovine serum)

Water: Sigma, Cat W4502 (water for molecular biology)

Ammonium acetate: Sigma, Cat A1542-250G (Ammonium acetate)

MES: Sigma, Cat M8250-25G (MES hydrate)

Ferrocyanide: Sigma, Cat P3289-100G (potassium ferrocyanide)

Glucose: Sigma, Cat G8270-1KG (D-(+)-Glucose)

HCl: Sigma, Cat H1758-100ML (hydrochloric acid, 36.5-38%)

NaOH: Sigma, Cat 72068 (sodium hydroxide solution)

HRP: BBI Enzymes, Cat HRP4C (Horseradish Peroxidase)

2MEA: Thermo Scientific, Cat 20408 (2-mercaptoethanolamine hydrochloride)

PSA standards (calibrated against WHO $1^{st}$ IRP (96/1670)): Perkin Elmer, Cat A073-301 (ProStatus PSA free/total kit, Delfia)

Biotin quantification kit: Thermo Scientific, Cat 28005 (Pierce biotin quantification kit)

Size exclusion columns: GE Healthcare, Cat 17-0851-01 (PD10 columns)

EDTA: Sigma, Cat EDS-100G (ethylenediamine tetracetic acid, anhydrous)

Tween: Sigma P7949-100ML (Tween-20)

DMSO: Thermo Scientific, Cat 20684 (dimethylsulfoxide)

Acetic acid: Sigma, Cat 32,009-9 (acetic acid)

Reagent Preparation

Antibody Biotinvlation.

Antibody Disulphide Bond Reduction

Antibody 1H12 and 5A6 are reduced using 2MEA in 1 mM EDTA in PBS, at 37 deg C. for 90 min. Reduced antibody is passed through a PD10 column and collected in 1 mM EDTA in PBS and fractions found to contain protein (by measurement at 280 nm on UV spectrophotometer) pooled. The concentration of reduced antibody is calculated using the extinction coefficient of the antibody of 1 mg/ml=1.4 absorbance units at 280 nm.

Binding of Maleimide-PEG2-biotin to Antibody

Maleimide-PEG2-biotin is added to the reduced antibody in molar excess to allow efficient binding to occur and incubated for 3 hours at room temperature. This is then passed through another PD10 column which has been pre-equilibrated with 1 mM EDTA in PBS, pH 7.2. 500 ul fractions are collected and measured using the UV spectrophotometer at 280 nm. The fractions containing significant protein levels are chosen and combined. A sample of this solution is measured again at 280 nm by absorbance, and the concentration of antibody determined using the extinction coefficient of the antibody of 1 mg/ml=1.4 absorbance units at 280 nm. The number of biotins bound per antibody are then determined using the Pierce biotin quantification kit, according to the manufacturer's instructions.

Latex.

Neutravidin Adsorption 10 um latex is washed in MES buffer (50 mM MES, pH 6.5) using centrifugation at 16100×g for 5 min at 4 deg C. to pellet the particles. The latex is resuspended at a concentration of 2% solids. Neutravidin is prepared at a concentration of 400 ug/ml in water. 2% latex and 400 ug/ml neutravidin are added together in equal volumes and mixed well. They are incubated for 18h with mixing on a rotary mixer (30 rpm) at room temperature. The particles are then washed in an equal volume of PBS (pH 7.2) 3 times (using centrifugation at 16100×g for 5 min, 4 deg C.) and resuspended in the same at a concentration of 2% solids.

Biotinylated GOD and biotinylated antibody 5A6 binding to latex 10 um latex is washed in 50 mM ammonium acetate, pH 4.2 (using centrifugation at 16100×g for 5 min, 4 deg C.) and resuspended in the same at a concentration of 1% solids. Biotinylated GOD is diluted in 50 mM ammonium acetate, pH 4.2 to a concentration of 160 ug/ml. Biotinylated antibody 5A6 is diluted to a concentration of 40 ug/ml in 50 mM ammonium acetate, pH 4.2. An equal volume of 40 ug/ml b5A6 is then added to 160 ug/ml bGOD. This mixture is then combined 1:1 with 1% neutravidin coated latex. This solution is mixed well and incubated for 30 min at room temperature with shaking on a rotary mixer (30 rpm).

The particles are then washed 4 times (using centrifugation at 16100×g, 5 min at 4 deg C.) with an equal volume of PBS, pH 7.2 to remove any unbound biotinylated GOD and biotinylated antibody and resuspended in PBS, pH 7.2 to give a latex concentration of 1% solids.

Paramagnetic Particles

Binding of Antibody to Particle 200 nm streptavidin coated paramagnetic particles are washed (using a magnetic separator) in 0.1% tween in PBS, pH 7.2 and resuspended in the same to give a concentration of 0.5% solids. Biotinylated antibody 1H12 is diluted in 0.1% tween in PBS, pH 7.2 to give 50 ug/ml. An equal volume of 0.5% paramagnetic particles and 50 ug/ml biotinylated antibody are combined, mixed and allowed to incubate for 30 min at room temperature, with shaking using a rotary shaker at 30 rpm.

The paramagnetic particles were then washed 4 times (using a magnetic separator) in an equal volume of 0.1% tween in PBS, pH 7.2 and resuspended in the same to give a concentration of paramagnetic particles of 1% solids.

Assay Procedure

Assay reagents were combined in the following volumes and concentrations into an eppendorf tube:

| | |
|---|---|
| 1% paramagnetic particles (with bound b1H12): | 2 ul |
| 150 mg/ml BSA, 0.25% tween all in PBS, pH 7.2: | 4 ul |
| 1% Latex (with bGOD and b5A6 bound): | 2 ul |
| PSA standard: | 2 ul |

All reagents added to eppendorf separately and kept separate in tube. All reagents finally combined by mixing upon addition of the:

| | |
|---|---|
| Reaction buffer: | 10 ul |

(Reaction buffer comprises 1M MES, pH 6.0, 200 mM glucose, 200 mM ferrocyanide, 2 mg/ml HRP)

These reagents are mixed thoroughly then 0.7 ul is added to a cartridge, which is connected up to a potentiostat (Autolab PGSTAT12). The cartridge is made up of a single channel, spanned by 2 screen-printed carbon electrodes (one working electrode and one counter/reference electrode) as shown in FIGS. 3 and 4. A measurement is made by a subtraction method, as follows.

Subtraction Assay

After 4.5 min incubation, the potentiostat changes from open circuit to −0.1V and the transient recorded with data points every 0.1 s. After an incubation of 5 min a magnet is applied to the cartridge in a way to remove the paramagnetic particle complexes from the working electrode (ie. on the opposite surface to the electrodes). The resultant transient is recorded for a further 5 min. The rate of reaction at the working electrode is calculated from the data obtained between around 200 s and 300 s after the potential step to −0.1V.

Summary of Assay Mechanism

In this assay mechanism (as summarised in FIG. 11), as soon as the reagents are combined, GOD converts glucose to gluconolactone with concurrent conversion of oxygen to hydrogen peroxide. The hydrogen peroxide then acts as a substrate for HRP which can then oxidise ferrocyanide to ferricyanide. The concentration of ferricyanide produced is therefore dependent upon the concentration of hydrogen peroxide produced which is itself dependent upon the concentration of GOD. The concentration of ferricyanide is measured by chronoamperometry, in this case by measuring the current produced at a potential of −0.1V between the working and counter/reference electrodes in a two electrode system. When the magnet is applied (away from the working electrode, on the opposite surface, directly above the working electrode) the paramagnetic particles will move to the magnet away from the vicinity of the working electrode. Depending upon the PSA concentration, some label particles which are coated in GOD will be removed also through their attachment to paramagnetic particles via PSA. In this case the concentration of GOD at the working electrode surface (where the measurement occurs) will then decrease in a manner dependent upon the number of label particles removed, which is dependent upon the concentration of PSA in the sample.

Results and Discussion

Figure 7:
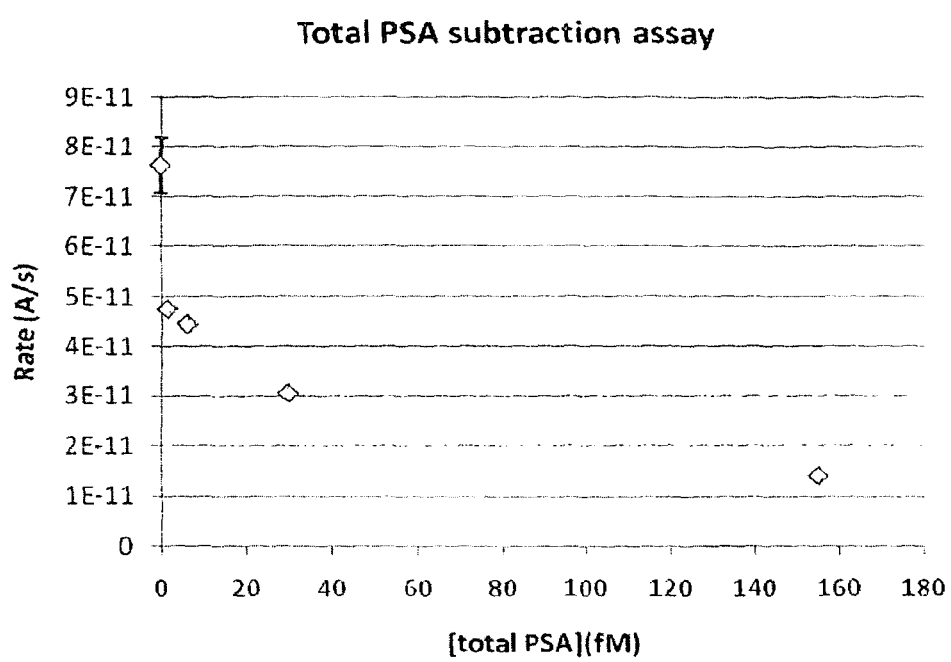
FIG. 7 shows graphed experimental results for the response of total PSA subtraction assay carried out with wet reagents in a test cartridge in accordance with the present invention.

FIG. 7 shows experimental results for the response of total PSA subtraction assay carried out with wet reagents in a test cartridge. The test used 0.7 ul volume and took a total of 10 min, in a buffer matrix. The 0 fM PSA result shows the mean of 4 separate measurements, carried out on different days with an error of 2 standard deviations. All other data points represent single measurements. The x axis represents the concentration of total PSA in fM. The y axis represents the reaction rate in A/s.

The data shown in FIG. 7 indicates that this assay format gives very high sensitivity, with levels well below 10 fM total PSA easily detectable from zero control. The data shows a measurable range of around 2 orders of magnitude (1.57-155 fM) with a curving response giving generally decreasing differentiation between points as the total PSA level increases.

In the subtraction assay, the rate decreases with increasing total PSA concentration as the magnet is removing paramagnetic particles complexed to electrochemical label via PSA away from the vicinity of the working electrode. As the rate is proportional to the concentration of the electrochemical label, this decreases as more of it is removed with increasing total PSA levels. It should be noted that the PSA samples used in this assay have been calibrated against the World Health Organisation (WHO) $1^{st}$ IRP (96/670) for total PSA.

The sensitivity and measurable range of this assay can be tuned by, for example, optimisation of reagent composition and concentration, as well as binding times and measurement times.

The way this assay has been measured there has been no correction for variations in background (caused by potential variation in reagent volume, working electrode area etc.). However, it is envisaged that a slight alteration of the measurement could allow an accurate background measurement to be made prior to the specific measurement for each sample in each channel. For example, this could be accomplished by starting the electrochemical measurement earlier at −0.1V (for example after 2 min incubation instead of 4.5 min) and allowing it to reach a steady rate prior to magnet application to the strip. Once the magnet is applied, this rate would change and the change in rate would be proportional to the PSA concentration, with the initial rate being the background measurement.

Here follows more experimental data generated by a specific embodiment of the current invention. The fluorescent detection of signal is made by a commercially available fluorescence plate reader (Perkin Elmer Victor3V) in place of the reader.

Fluorescent Dry Assay of Free PSA

Materials:

Maleimide-PEG2-biotin: Thermo Scientific, Cat 21901 (EZ-link maleimide-PEG2-biotin).

Latex particles: invitrogen, Cat F8827 (FluoSpheres, carboxylate modified microspheres, 2 μm, yellow-green fluorescent)

Paramagnetic particles : Ademtech, Cat 03223 (200 nm Strep+ magnetic particles)

Antibody 8A6: Hytest, Cat 4P33 MAb 8A6 (Anti-PSA, human)

Antibody 5A6: Hytest, Cat 4P33 MAb 5A6 (Anti-PSA, human)

PBS: Thermo Scientific, Cat 28372 (BupH phosphate buffered saline packs)

BSA: Sigma, Cat A4503-50 G (Albumin, from bovine serum)

Water: Sigma, Cat W4502 (water for molecular biology)

Trehalose: Sigma, Cat T9531-25G (D-(+)-trehalose dehydrate)

MES: Sigma, Cat M8250-25G (MES hydrate)

HCl: Sigma, Cat H1758-100ML (hydrochloric acid, 36.5-38%)

NaOH: Sigma, Cat 72068 (sodium hydroxide solution)

2MEA: Thermo Scientific, Cat 20408 (2-mercaptoethanolamine hydrochloride)

PSA standards (calibrated against WHO $1^{st}$ IRP (96/670)): Perkin Elmer, Cat A073-301 (ProStatus PSA free/total kit, Delfia)

Biotin quantification kit: Thermo Scientific, Cat 28005 (Pierce biotin quantification kit)

Size exclusion columns: GE Healthcare, Cat 17-0851-01 (PD10 columns)

EDTA: Sigma, Cat EDS-100G (ethylenediamine tetracetic acid, anhydrous)

Tween: Sigma P7949-100 ML (Tween-20)

DMSO: Thermo Scientific, Cat 20684 (dimethylsulfoxide)

Acetic acid: Sigma, Cat 32,009-9 (acetic acid)

Reagent Preparation
Antibody Biotinylation.
Antibody 8A6 Disulphide Bond Reduction Use undiluted antibody 8A6 stock at a concentration between 2 and 7 mg/ml. An appropriate volume of antibody stock is removed to give 1 mg antibody. An appropriate volume of 14.28 mM EDTA in PBS, pH 7.2 is added to 1 mg antibody to give an EDTA concentration of 1 mM.

6 mg of 2MEA is dissolved in 100 ul 1 mM EDTA in PBS, pH 7.2. 1 ul of this 2MEA solution is added per 10 ul of antibody solution. This solution is mixed and incubated in a waterbath at 37 deg for 90 min.

This solution is then passed through a PD10 column (pre-equilibrated with 1 mM EDTA in PBS, pH 7.2) and 500 ul fractions collected. A sample from each fraction is taken and measured on UV spectrophotometer, with the absorbance at 280 nm used to quantify the protein found in each fraction. The fractions containing significant concentrations of protein are chosen and combined and remeasured on the UV spectrophotometer. This measurement is used to determine the antibody concentration using an extinction coefficient of the antibody of 1 mg/ml=1.4 absorbance units at 280 nm.

Binding of Maleimide-PEG2-Biotin to Antibody

Maleimide-PEG2-biotin is dissolved in 1 mM EDTA in PBS, ph7.2 to give a 20 mM solution. An appropriate volume of this is added to the reduced antibody to give a 40 times molar excess of maleimide-PEG2-biotin over reduced antibody. This is then mixed and incubated for 3 hours at room temperature.

This is then passed through another PD10 column which has been pre-equilibrated with 1 mM EDTA in PBS, pH 7.2. 500 µl fractions are collected and measured using the UV spectrophotometer at 280 nm. The fractions containing significant protein levels are chosen and combined. A sample of this solution is measured again at 280 nm by absorbance, and the concentration of antibody determined using the extinction coefficient of the antibody of 1 mg/ml=1.4 absorbance units at 280 nm. The number of biotins bound per antibody are then determined using the Pierce biotin quantification kit, according to the manufacturer's instructions.

Latex.
Antibody Adsorption

2 µm latex is washed in MES buffer (50 mM MES, pH 6.5) using centrifugation at 16100×g for 8 min at 4 deg C. to pellet the particles. The latex is resuspended at a concentration of 2% solids. Antibody 5A6 is prepared at a concentration of 250 µg/ml in MES buffer. 2% latex and 250 µg/ml antibody are added together in equal volumes and mixed well. They are incubated for 18h with mixing on a rotary mixer (30 rpm) at room temperature. The particles are then washed in an equal volume of PBS (pH 7.2) 3 times (using centrifugation at 16100×g for 8 min, 4 deg C.) and resuspended in the same at a concentration of 2% solids.

Paramagnetic Particles
Binding of Antibody to Particle 200 nm streptavidin coated paramagnetic particles are washed (using a magnetic separator) in 0.1% tween in PBS, pH 7.2 and resuspended in the same to give a concentration of 0.5% solids. Biotinylated antibody 8A6 is diluted in 0.1% tween in PBS, pH 7.2 to give 50 µg/ml. An equal volume of 0.5% paramagnetic particles and 50 µg/ml biotinylated antibody are combined, mixed and allowed to incubate for 30 min at room temperature, with shaking using a rotary shaker at 30 rpm.

The paramagnetic particles were then washed 4 times (using a magnetic separator) in an equal volume of 0.1% tween in PBS, pH 7.2 and resuspended in the same to give a concentration of paramagnetic particles of 1% solids.

Reagent Deposition

Reagents were diluted and combined to give a final deposition solution containing the following:

0.02% latex particles functionalised with antibody 5A6, in PBS, pH 7.2

0.1% paramagnetic particles functionalised with antibody 8A6, in PBS, pH 7.2

180 mg/ml BSA, in PBS, pH 7.2

1 mg/ml trehalose, in PBS, pH 7.2

The cartridge used for the dry assay was that as shown in FIG. 2, except without any electrodes on the base (23). The base layer (20) and adhesive layer (21) were combined and even pressure applied to seal these layers together to form a half assembled cartridge.

0.5 ul of deposition solution was deposited within a channel (24) of the half assembled cartridge by pipette.

This was dried at 40 deg C. for 30 min.

The lid (22) was then applied to the half assembled cartridge and even pressure applied to seal the fully formed cartridge, complete with dried reagents within the channel.

Assay Procedure 2.5 ul of PSA standard was then applied to the cartridge to fill the 4 channels and resuspend the dried reagents.

The cartridge was incubated at room temperature for 8 minutes to allow the binding reaction to occur.

The cartridge was placed on a custom built holder to allow measurement within a channel by a Perkin Elmer Victor3 V.

The fluorescent signal in the channel was measured using the inbuilt program 'Fluorescein (485 nm/535 nm, 0.1s)'. This program uses excitation at 485 nm and emission at 535 nm with a 0.1 s measurement time. This signal was recorded as Fln 1.

A magnet was then applied to the cartridge to remove the paramagnetic particles (and any paramagnetic particle-bound components) from the channel.

The fluorescent signal in the channel was then re-measured using the inbuilt program 'Fluorescein (485 nm/535 nm, 0.1s)', This signal was recorded as Fln 2.

Figure 8:
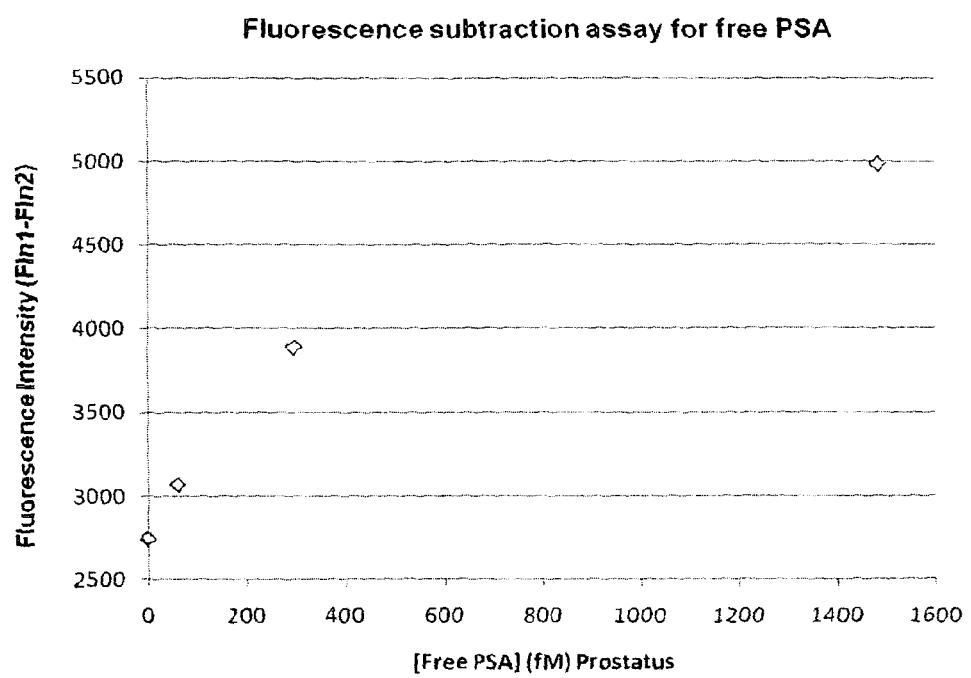
FIG. 8 shows graphed experimental results for the response of an assay for free PSA carried out with dried reagents and fluorescent detection in a test cartridge in accordance with the present invention.

The difference in the two signals (Fln 1-Fln 2) was calculated and the results graphed against free PSA concentration as shown in FIG. 8.

Results and Discussion

The data shown in FIG. 8 indicates that the fluorescent assay format gives high sensitivity, with free PSA concentration of 58 fM detectable from zero control. The data shows a measurable range of around 2 orders of magnitude (58-5000 fM) with a curving response giving generally decreasing differentiation between points as the total PSA level increases.

In this subtraction assay, the Fln 1 signal is independent of PSA concentration whereas the Fln 2 signal decreases with increasing free PSA concentration as the magnet is removing paramagnetic particles complexed to fluorescent label via PSA from the channel. The difference between these signals therefore increases as the PSA concentration increases.

It should be noted that the PSA samples used in this assay have been calibrated against the World Health Organisation (WHO) $1^{st}$ IRP (96/670) for total PSA.

The sensitivity and measurable range of this assay can be tuned by, for example, optimisation of reagent composition and concentration, as well as binding times and excitation and emission wavelenths.

The way this assay and the other assays described herein, has been measured, by using the difference between two measurements corrects the signal for variations in background (caused by potential variation in reagent volume, working electrode area etc.). This allows a more sensitive and accurate measurement to be made.

Here follows more experimental data generated in support of the advantages of a specific embodiment of the current invention.

Method Development

A further method has been developed to measure the label glucose oxidase (GOD) (or other enzyme labels) in the described subtraction assay method whereby magnetic particle bound label is removed from the detection area. The unbound GOD label is therefore measured and used to assign analyte concentration. The GOD label concentration is measured before magnetic separation/removal of the bound GOD label from the detection zone. The two measurements are then used to calculate the relative change in label concentration and assign analyte concentration.

Figure 11:
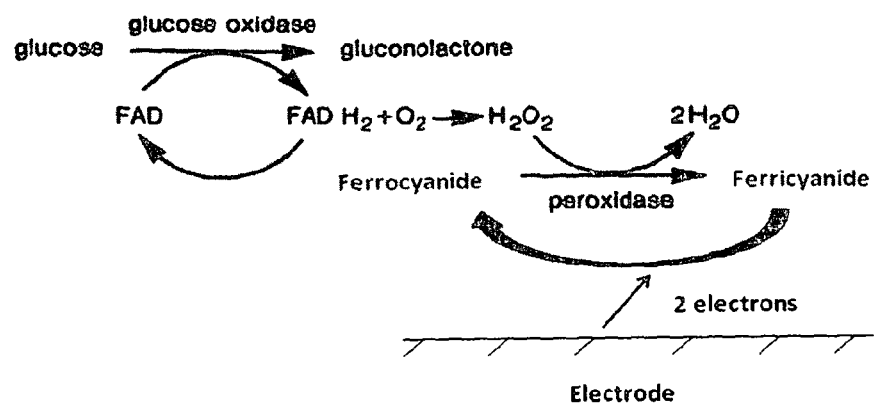
FIG. 11 shows a reaction mechanism of a desired embodiment of the present invention.

During the assay binding time the enzymatic reaction is simultaneously occurring (all events occurring in the detection zone). An example GOD detection cascade is shown in FIG. 11 using ferrocyanide conversion into ferricyanide by peroxidase using hydrogen peroxide, In the examples discussed in this section from here onwards, ABTS is used in the GOD detection cascade instead of ferrocyanide, and is converted to oxidised ABTS by peroxidase using hydrogen peroxide. In this example, therefore, the GOD detection cascade is producing oxidised ABTS during the assay binding time (e.g. for 4 minutes). Therefore changes of GOD label concentration after the magnetic removal of GOD label-magnetic particle analyte complex from the detection zone are being determined on a larger background current. In previous examples we have used rate measurements to make highly accurate measurements of GOD concentration and hence analyte concentrations. We have developed an additional electrochemical method that also produces very accurate measurements of GOD concentrations.

Figure 16:
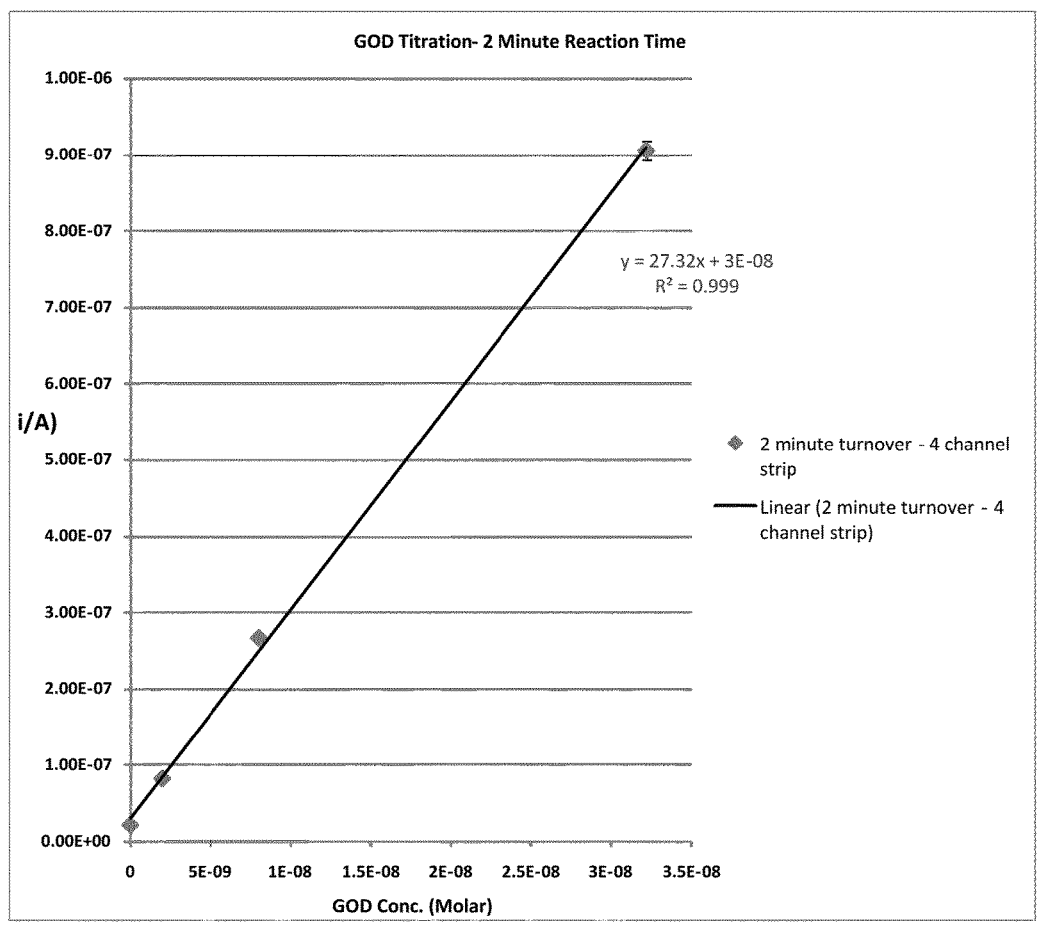
FIG. 16 shows a typical graphed GOD titration curve whereby the current value plotted is extracted from the 3 second point of a 3 second chronoamperometric transient after the GOD was allowed to react with the substrate system for 2 minutes.

A typical GOD titration curve is shown in FIG. 16 whereby the current value plotted is extracted from the 3 second point of a 3 second transient, the GOD was allowed to react with the substrate system for 2 minutes before a chronoamperometric measurement was performed. A linear response is observed. The four channel strip (as shown in FIG. 15) was used for these measurements.

Therefore after 2 minutes of enzymatic reaction, a defined GOD concentration will produce a certain current. If we allowed the enzymatic reaction to occur for another two minutes the currents produced for a defined GOD concentration would be larger. Therefore post magnetic separation unbound GOD label concentrations are determined on large background currents (4 minutes of enzymatic reaction during the 4 minutes of assay binding). We have therefore developed the following technique to counteract this scenario.

To prevent large amounts of oxidised ABTS being created by GOD, an electrochemical potential is applied to the electrodes for the duration of the assay binding (e.g. 4 mins). In this example a −350 mV potential is applied however the appropriate potential for any enzyme/mediator system could be used. The −350 mV potential applied to the strip during 4 minutes allows for 2 fundamental processes to occur. Firstly it allows a measure of GOD label concentration and secondly it significantly reduces the amount of oxidised ABTS created during the 4 minute assay binding time (and hence the current magnitude upon which GOD label concentrations are measured).

Figure 17:
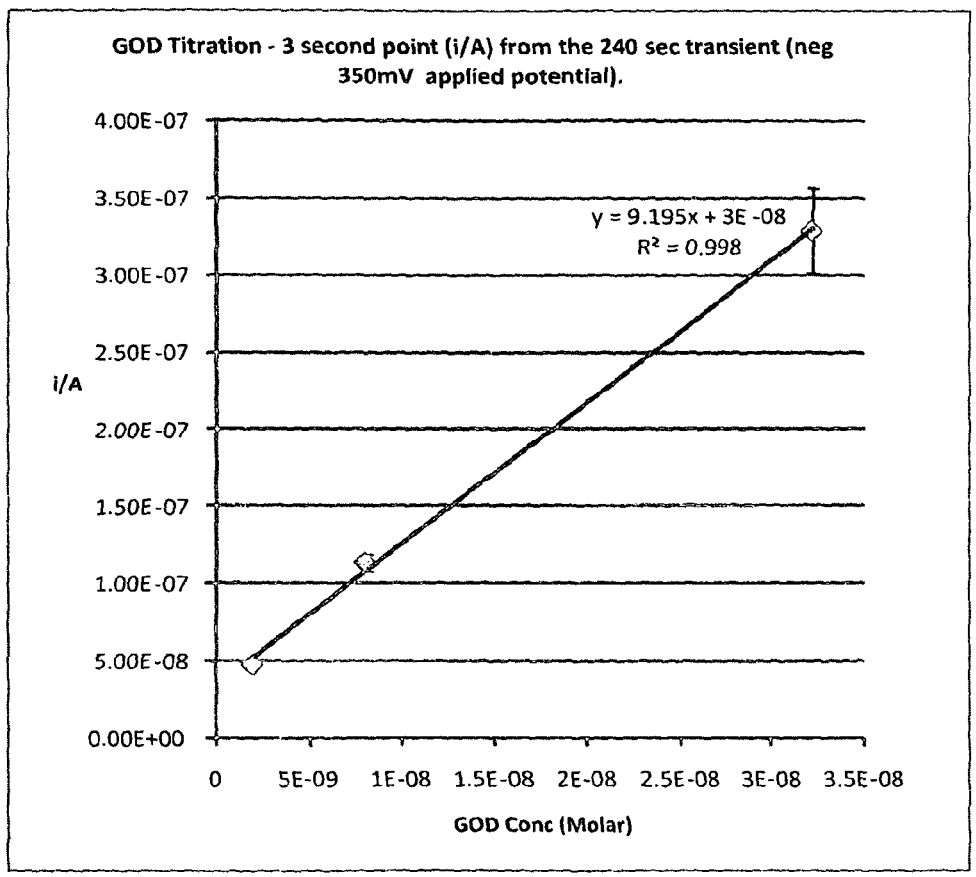
FIG. 17 shows a graphed GOD titration whereby the current value plotted is extracted from the 3 second point of a 240 second transient.

A GOD titration response is shown in FIG. 17 whereby the current value plotted is extracted from the 3 second point of a 240 second transient. This response can therefore be used to assign GOD concentrations or in the context of the immunoassay procedure, a measure of GOD label concentration pre magnetic separation (i.e. before the removal of magnetic particle bound GOD). This GOD concentration is then used in conjunction with the final unbound GOD label concentration to correct for variations in GOD label concentrations.

Figure 18:
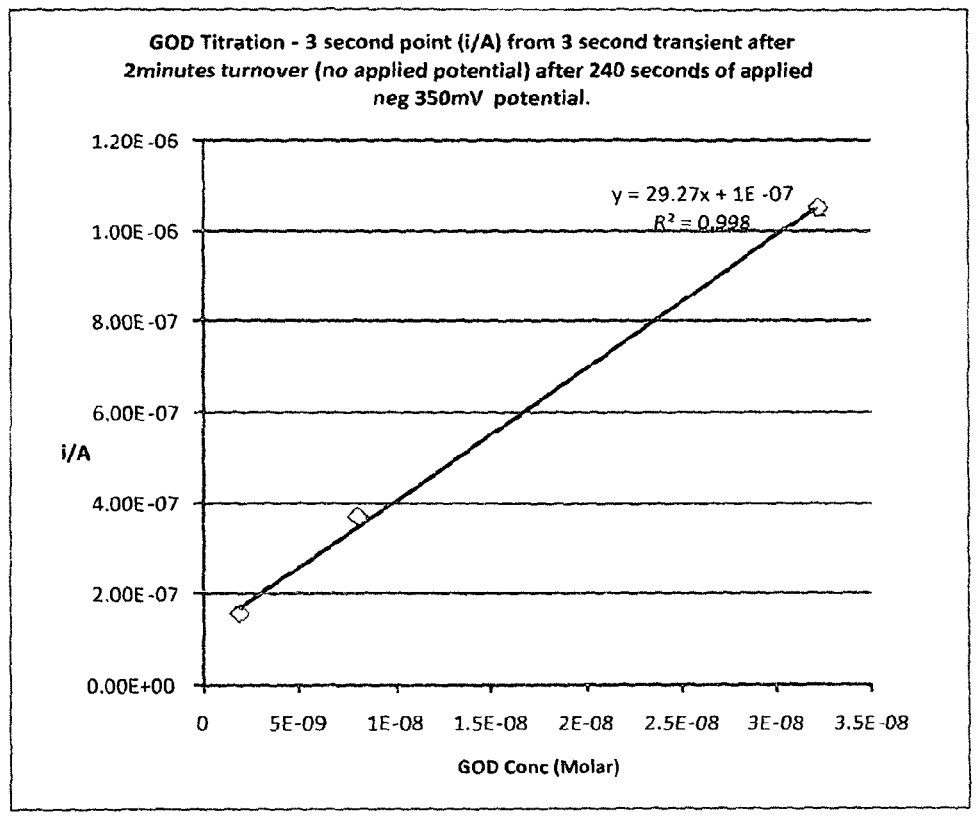
FIG. 18 shows a graphed GOD titration measured at −350V after a 2 min reaction following a 4 min incubation at an applied potential of −350mV.

Although the 3 sec time point measurement is used from the 240 sec transient generated, any timepoint from within this transient could be used to assign GOD concentration. After 240 seconds the −350 mV potential is switched off and the strip returns to open circuit potential (OCP). In the example we describe here the GOD reaction was allowed to occur for 2 minutes (OCP, no applied potential), a 3 second chronoamperometric measurement was then performed. The 3 sec current value from the 3 sec transient was then plotted vs. GOD concentrations (see FIG. 18). A linear, very accurate response is observed. This measurement represents the post magnetic separation measurement of unbound GOD label concentration. This post magnetic separation GOD label concentration and the pre magnetic separation GOD concentration would be used together to determine the analyte concentration.

Figure 19:
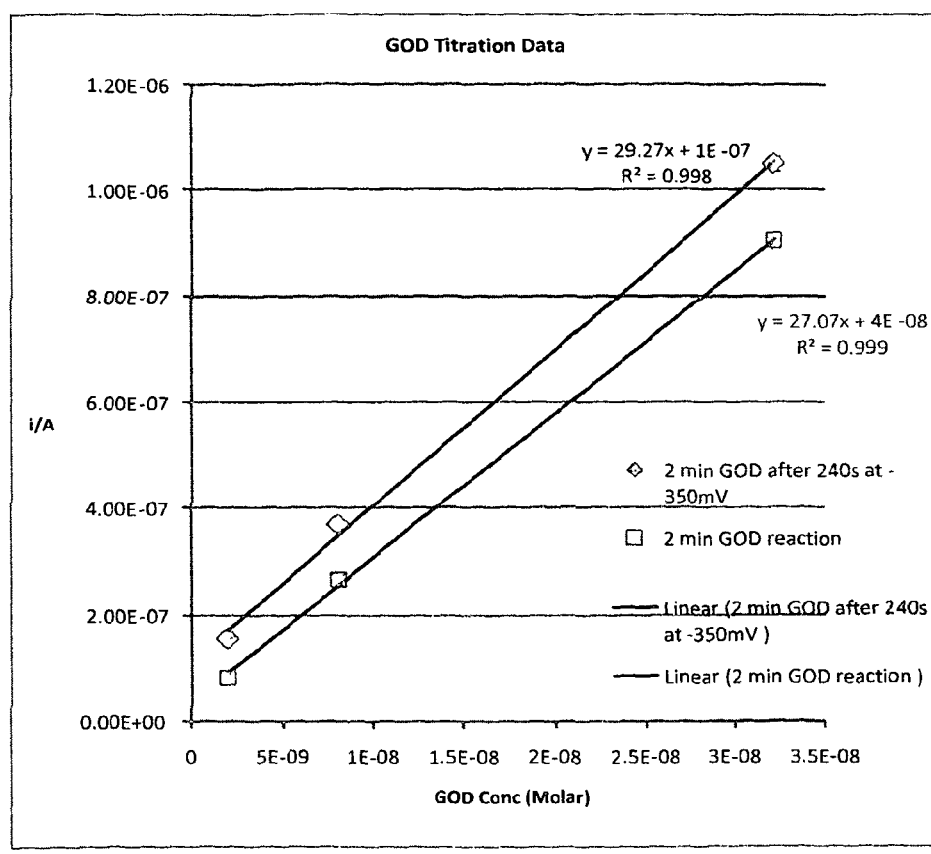
FIG. 19 shows a graph comparing GOD titration curves for a normal 2 minute GOD titration and a 2 minute titration after the applied −350mV potential for 4 minutes.

The GOD titration curves for a normal 2 minute GOD titration and a 2 minute titration after the applied −350 mV potential for 4 minutes (240 sec) are both shown in FIG. 19. The responses are very similar. The small offset between the responses is driven by differences in electrochemical background currents and small amount of oxidised ABTS that will be accumulated during the 240 secs of applied −350 mV potential. If the 240 secs of −350 mV potential had not been applied, the comparison would be 6 minutes of total GOD turnover vs. 2 minutes of GOD reaction. In the context of the assay scheme this would be measuring post magnetic separation GOD concentrations with 4 minutes of current generated during the pre magnetic separation stage of the assay binding time.

This measurement methodology was then applied to an immunoassay measurement of Total PSA to demonstrate the utility of the measurement. The experiment was combined with reagent changes to show increases in the dynamic range of the PSA assay.

Here follows more experimental data generated by a specific embodiment of the current invention. The electrochemical detection of signal is made by a commercially available potentiostat, in place of the reader.

Electrochemical Assay of Total PSA (II)

Materials:

PSA: Hytest, Cat 8P78 (Prostate Specific Antigen)

ABTS: Fluka, Cat 11557

Zeba size exclusion columns: ThermoFisher Scientific, Cat 89882

SPDP: Pierce, Cat 21857

GOD:BBI Enzymes, Cat GO3B3 (Glucose oxidase)

Maleimide-PEG2-biotin: Thermo Scientific, Cat 21901 (EZ-link maleimide-PEG2-biotin).

Latex particles: lnvitrogen, Cat F8765 (1 um)

Paramagnetic particles : Ademtech, Cat 03223 (200 nm Strep+paramagnetic particles)

Antibody 1H12: Hytest, Cat 4P33 MAb 1H12 (Anti-PSA, human)

Antibody 5A6: Hytest, Cat 4P33 MAb 5A6 (Anti-PSA, human)

PBS: Thermo Scientific, Cat 28372 (BupH phosphate buffered saline packs)

BSA: Sigma, Cat A4503-50 G (Albumin, from bovine serum)

Water: Sigma, Cat W4502 (water for molecular biology)

MES: Sigma, Cat M8250-25 G (MES hydrate)

Glucose: Sigma, Cat G8270-1 KG (D-(+)-Glucose)

DTT : Pierce, Cat 20290

HCl: Sigma, Cat H1758-100 ML (hydrochloric acid, 36.5-38%)

NaOH: Sigma, Cat 72068 (sodium hydroxide solution)

HRP: BBI Enzymes, Cat HRP4C (Horseradish Peroxidase)

2MEA: Thermo Scientific, Cat 20408 (2-mercaptoethanolamine hydrochloride)

Biotin quantification kit: Thermo Scientific, Cat 28005 (Pierce biotin quantification kit)

Size exclusion columns: GE Healthcare, Cat 17-0851-01 (PD10 columns)

EDTA: Sigma, Cat EDS-100G (ethylenediamine tetracetic acid, anhydrous)

Tween: Sigma P7949-100 ML (Tween-20)

DMSO: Thermo Scientific, Cat 20684 (dimethylsulfoxide)

Reagent Preparation

Antibody Biotinylation.

Antibody Disulphide Bond Reduction

Antibody 1H12 is reduced using 50 mM 2 MEA in 1 mM EDTA in PBS, at 37 deg C. for 90 min. Reduced antibody is passed through PD10 column and collected in 1 mM EDTA in PBS and fractions found to contain protein (by measurement at 280 nm on UV spectrophotometer) pooled. The concentration of reduced antibody is calculated using the extinction coefficient of the antibody of 1 mg/ml =1.4 absorbance units at 280 nm.

Binding of Maleimide-PEG2-Biotin to Antibody

Maleimide-PEG2-biotin is added to the reduced antibody in molar excess to allow efficient binding to occur and incubated for 3 hours at room temperature. This is then passed through another PD10 column which has been pre-equilibrated with 1 mM EDTA in PBS, pH 7.2. 500 ul fractions are collected and measured using the UV spectrophotometer at 280 nm. The fractions containing significant protein levels are chosen and combined. A sample of this solution is measured again at 280 nm by absorbance, and the concentration of antibody determined using the extinction coefficient of the antibody of 1 mg/ml=1.4 absorbance units at 280 nm. The number of biotins bound per antibody are then determined using the Pierce biotin quantification kit, according to the manufacturer's instructions.

Latex.

Binding of GOD/1H12 to Latex via SPDP

Latex particles are bound to SPDP in 1 mM EDTA in PBS buffer at a concentration of 1% solids and 1 mM SPDP. This is incubated with gentle shaking for 90 min at room temperature in the dark. GOD/5A6 conjugate is bound to SPDP using a molar excess of SPDP:GOD/1H12 and incubated for 90 min at room temperature in the dark. After 90 min a proportion of the GOD/5A6-SPDP is reduced by the addition of DTT at pH 4.5 with a further 30 min incubation at room temperature in the dark. After the specified binding time, the latex particles are washed into 1 mM EDTA in PBS buffer at a concentration of 1% solids (using centrifugation and sonnication for pelleting and resuspension respectively). The GOD/5A6-SPDP reactions are passed through a Zeba desalting column and collected in 1 mM EDTA in PBS. The latex-SPDP and GOD/5A6-SPDP are then combined to give an excess of GOD/5A6-SPDP to latex-SPDP binding sites. This binding reaction is incubated for 19 h at room temperature with gentle shaking in the dark. This binding reaction is then washed into 0.1% tween in PBS and resuspended at 1% solids and stored at +4 deg C. in the dark until use.

Paramagnetic Particles

Binding of Antibody to Particle 200 nm streptavidin coated paramagnetic particles are washed (using a magnetic separator) in 0.1% tween in PBS, pH 7.2 and added to biotinylated antibody 1H12 to allow binding of the biotin of the biotinylated antibody to the streptavidin-coated paramagnetic particle, with a 1h10 min incubation at room temperature with gentle shaking. The paramagnetic particles are then washed 4 times (using a magnetic separator) in an equal volume of PBS, pH 7.2 and resuspended in the same to give a concentration of paramagnetic particles of 1% solids which are stored at +4 deg C. until use.

Assay Procedure

Assay reagents were added to an eppendorf tube in the following volumes and concentrations:

| | |
|---|---|
| 1% paramagnetic particles (with bound b1H12): | 1 ul |
| 1% Latex (with bGOD and b5A6 bound): | 1 ul |
| PSA (10x final concentration in 300 mg/ml BSA in PBS): | 1 ul |

All reagents added to eppendorf separately and kept separate in tube. All reagents finally combined by mixing upon addition of the:

| | |
|---|---|
| Reaction buffer: | 7 ul |

(Reaction buffer comprises 500 mM MES, pH 6.7, 250 mM glucose, 15 mM ABTS, 4 mg/ml HRP, 0.14% tween)

These reagents are mixed thoroughly then 4 ul is added to a cartridge, which is connected up to a potentiostat (Autolab PGSTAT12). The immunoassay reaction contains all the reagents for the binding reaction (anti-PSA antibody magnetic particles, PSA analyte, anti-PSA antibody-GOD label) and all the reagents for the enzymatic reaction (glucose, HRP, ABTS).The cartridge is made up of 4 channels, with 3 channels each spanned by 2 screen-printed carbon electrodes (one working electrode and one counter/reference electrode) and 1 channel being spanned by 2 screen printed silver/silver chloride electrodes as shown in FIGS. 1 and 15. Measurements were carried out in the 3 channels with screen printed carbon electrodes in this experiment, as follows:

Experimental Methodology

As soon as the reagents are mixed the binding and enzymatic reaction begin. This all occurs in the detection zone. After 30 seconds a negative 350 mV potential is applied to the strip for 240 seconds (as shown in the transient). The 3 second current value from the 240 sec transient is recorded (other points from the transient could be used). This value represents a measure of the anti-PSA antibody-GOD label concentration at the detection zone (working electrode) of the strip and is called the pre magnetic separation current/measurement. After 210 seconds the magnetic is applied to the strip. The anti-PSA antibody magnetic particles-PSA- anti-PSA antibody-GOD label complexes are removed from the detection zone leaving behind unbound anti-PSA antibody-GOD label. The −350 mV potential is switched off after 240 seconds (after the magnetic separation step) returning the detection zone/strip to OCP. The strip remains at OCR for 2 minutes before a chronoamperometric measurement is performed. The 3 second current value from a 3 second transient was then recorded; this is called the post magnetic separation current/measurement. This procedure was repeated for all the PSA concentrations assayed.

Results and Discussion

Figure 20:
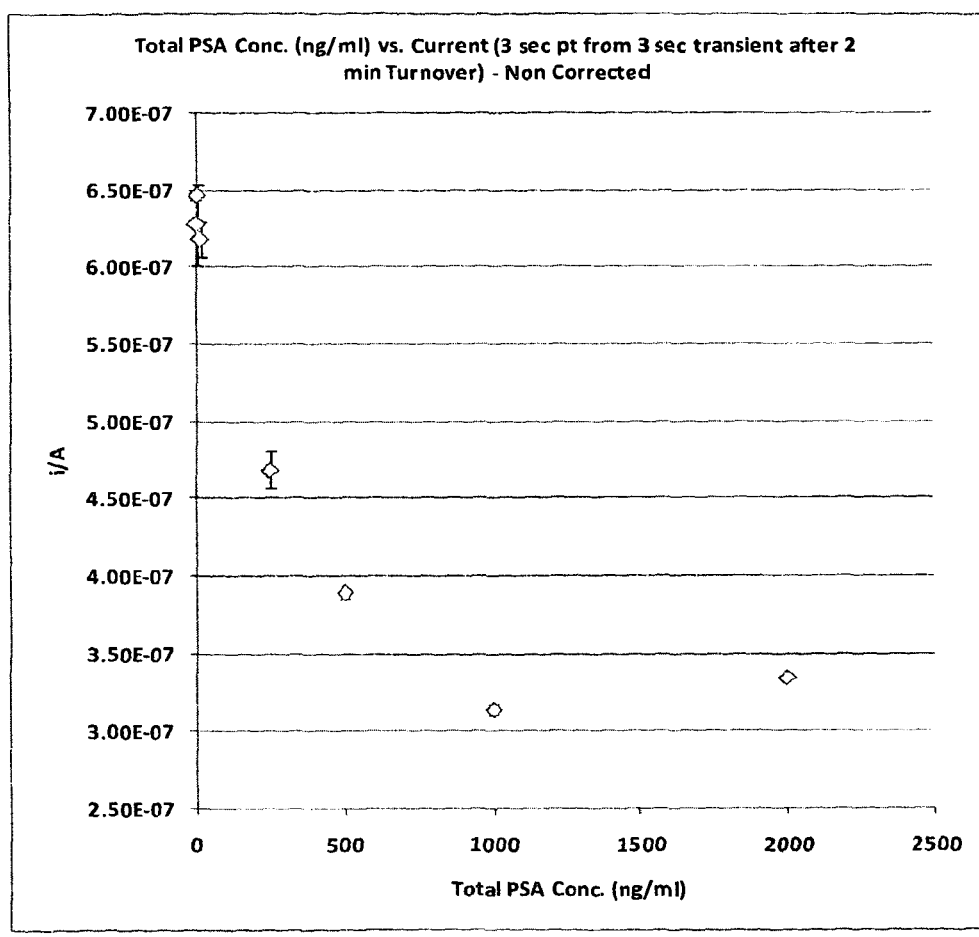
FIG. 20 shows a graph of the uncorrected post magnetic separation measurement of PSA concentration in accordance with the present invention.

The non corrected post magnetic separation measurement of PSA concentration is shown in FIG. 20. A systematic decrease in current is observed as the concentration of PSA is increased. The precision is fairly good however at low PSA concentrations although the means are systematic with PSA concentration the associated error is bad.

Figure 22:
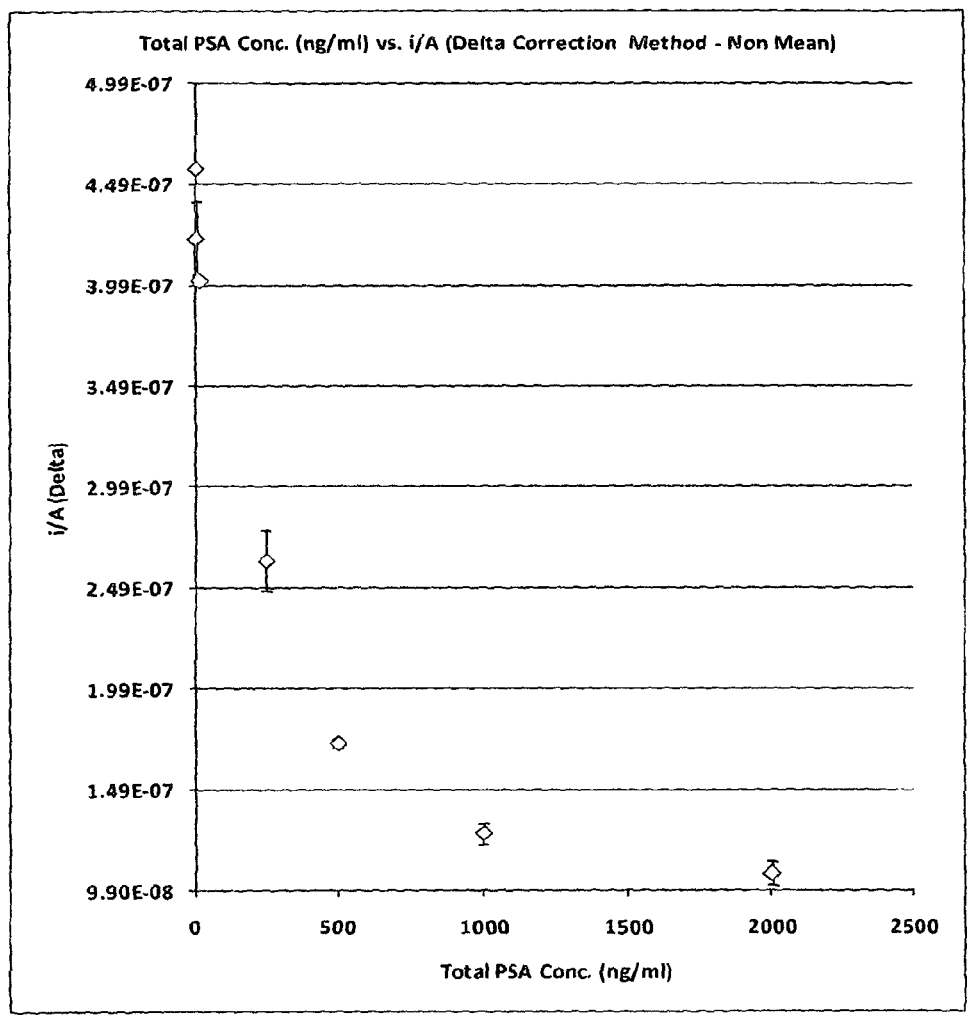
FIG. 22 shows a graph of the difference between post magnetic separation current and the pre magnetic separation current for all concentrations of PSA in accordance with the current invention.

The variation in the PSA assay results are driven by variations in the pre magnetic separation current/measurement. This is shown in the following analysis. The difference between post magnetic separation current and the pre magnetic separation current for all concentrations and reps are shown in FIG. 21. This data is graphically represented in FIG. 22

Figure 24:
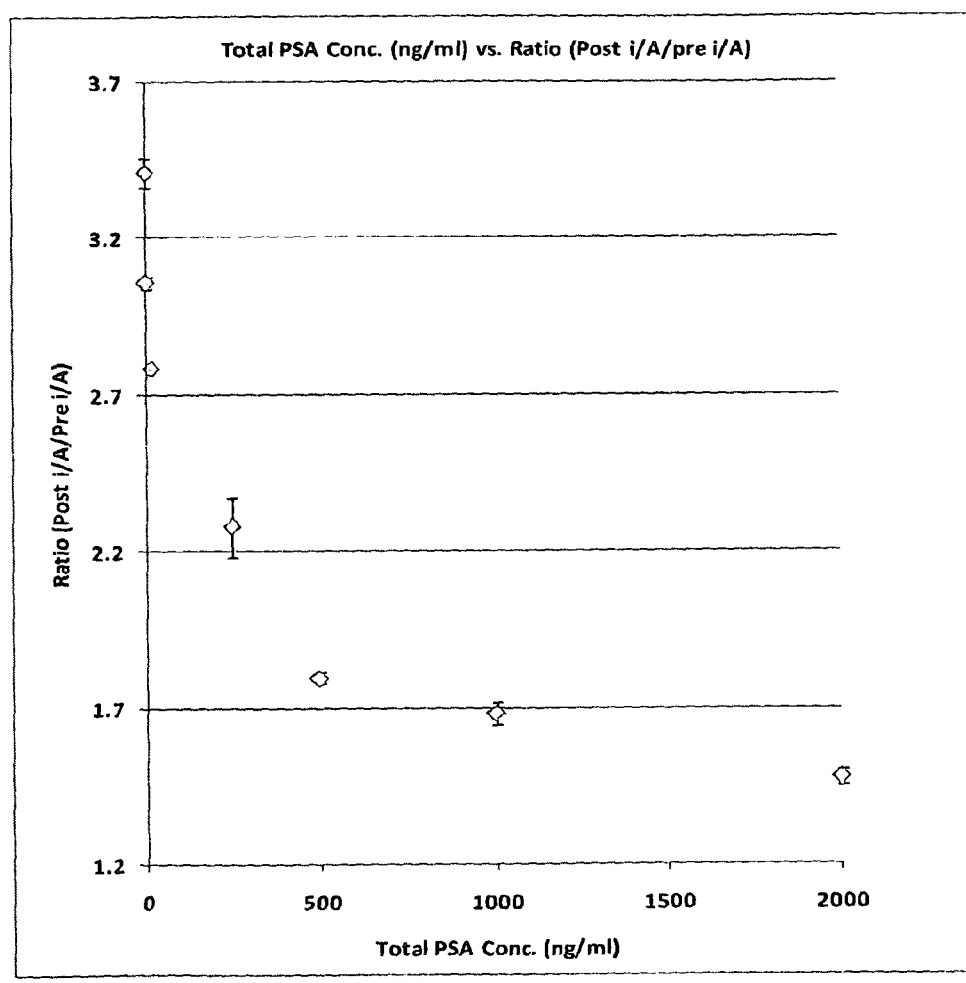
FIG. 24 shows a graph of the ratio of the post magnetic separation current to the pre magnetic separation current in accordance with the current invention.

The PSA assay performance has improved compared to the uncorrected post magnetic separation current with increased sensitivity and overall precision. The PSA assay improves further when the proportionality of change between post magnetic separation current and pre magnetic separation current are taken into consideration. The ratio of the post magnetic separation current to the pre magnetic separation current is shown in FIG. 23, the graphically representation of this data is shown in FIG. 24. The PSA performance improves further with regards to sensitivity and precision. Although the majority of the pre magnetic separation current discussion is based around the influence of anti-PSA antibody-GOD label, we fully recognise the pre magnetic response/current used for normalisation is the result of the interplay of all inputting factors (anti-PSA antibody-GOD label, working electrode size, mediator concentrations, cell height, HCT, etc) and therefore used to correct for many sources of assay variation.

Figure 25:
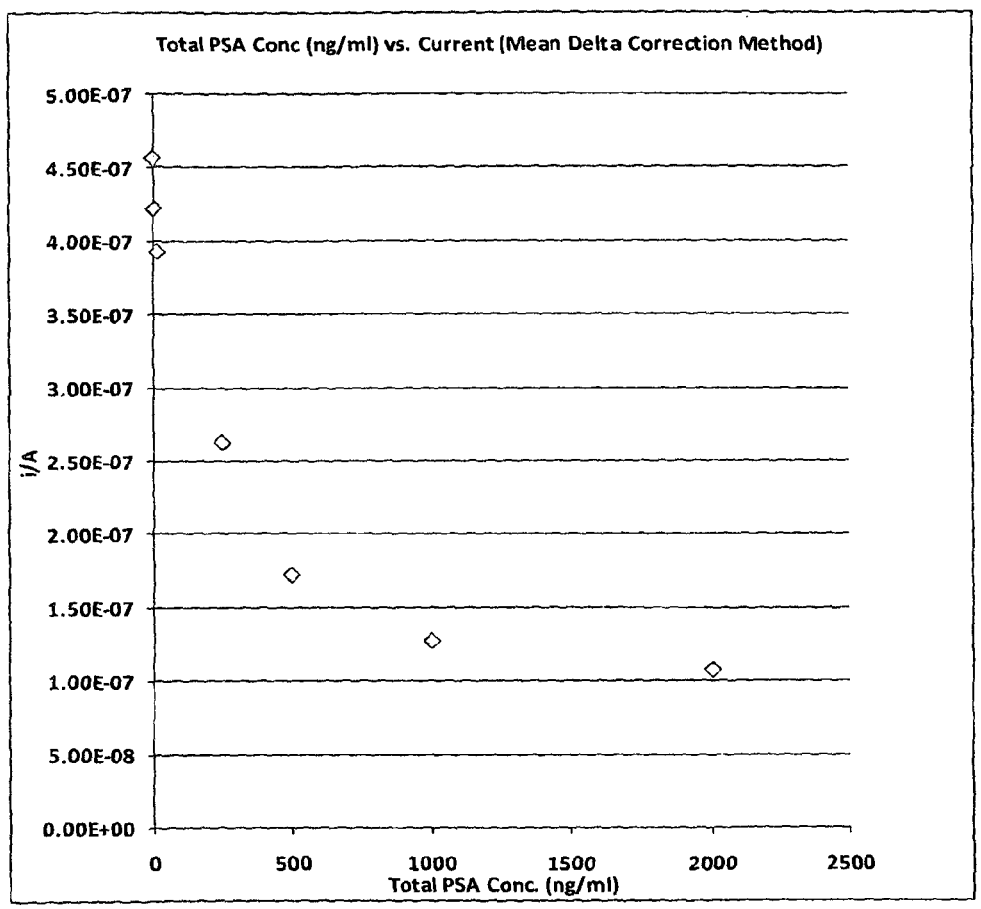
FIG. 25 shows a graph of the difference between the mean pre magnetic separation current and the post magnetic separation current in accordance with the current invention.

The strip format (4 channel, 20 channel etc) allows multiple measurements of the same analyte to be made or multiple measurements of the same analyte made. Even a crude correction of subtracting the mean pre magnetic separation current (three measurements within a strip) from the mean post magnetic separation current (three measurements within a strip) improves assay performance (see FIG. 25). In this context although the assay has been used to measure the analyte 3 times (within one strip) a mean response would be used to determine the analyte/PSA concentration of the sample. As a result very accurate measurements on analyte dose will be observed, due to precision improvements within a measurement (this is discussed elsewhere in the document). However even in a mean crude correction methodology a measurement of the pre magnetic separation current is very beneficial.

Here follows more experimental data generated by a specific embodiment of the current invention. The electrochemical detection of signal is made by a commercially available potentiostat, in place of the reader.

Electrochemical Assay of Total PSA (III)

Materials:

EDC: Sigma, Cat 03449
Sulfo-NHS: ThermoFisher Scientific, Cat 24510
Latex particles: Invitrogen, Cat F8827 (2 um, COOH surface)
Antibody 1H12: Hytest, Cat 4P33 MAb 1H12 (Anti-PSA, human)
Antibody 5A6: Hytest, Cat 4P33 MAb 5A6 (Anti-PSA, human)
GOD: BBI Enzymes, Cat GO3B3 (Glucose oxidase)
Paramagnetic particles : Chemicell, 500 nm SiMag-Carbonyl
PBS: Thermo Scientific, Cat 28372 (BupH phosphate buffered saline packs)
BSA: Sigma, Cat A4503-50G (Albumin, from bovine serum)
Water: Sigma, Cat W4502 (water for molecular biology)
Sodium acetate : Sigma, Cat 58750
MES: Sigma, Cat M8250-25G (MES hydrate)
Tris : Sigma , Cat 93362 (Trizma base)
Ferrocyanide: Sigma, Cat P3289-100 G (potassium ferrocyanide)
Glucose: Sigma, Cat G8270-1KG (D-(+)-Glucose)
HCl: Sigma, Cat H1758-100 ML (hydrochloric acid, 36.5-38%)
NaOH: Sigma, Cat 72068 (sodium hydroxide solution)
HRP: BBI Enzymes, Cat HRP4C (Horseradish Peroxidase)
PSA: Hytest, Cat 8P78 (Prostate Specific Antigen)
EDTA: Sigma, Cat EDS-100G (ethylenediamine tetracetic acid, anhydrous)
Tween: Sigma P7949-100 ML (Tween-20)
DMSO: Thermo Scientific, Cat 20684 (dimethylsulfoxide)
Acetic acid: Sigma, Cat 32,009-9 (acetic acid)
Trehalose: Sigma, Cat T9531 (D-(+)-trehalose dihydrate)

Reagent Preparation

Latex Binding to GOD and 5A6 using EDC

Incubate 1% latex particles with 20 mg/ml EDC and 20 mg/ml suifo-NHS, all in 50 mM MES buffer, pH 6.0 for 20 min at room temperature in the dark. Wash latex particles in 50 mM sodium acetate, pH 4.6 and resuspend in same at 1% solids.

Add latex-EDC to GOD and 5A6 antibody to give final concentrations of 0.5% latex, 1.5 mg/ml GOD and 0.5 mg/ml 5A6 all in 50 mM sodium acetate, pH 4.6. Incubate for 3h10 min at room temperature with gentle shaking.

Wash latex particles in 50 mM tris buffer, pH7.1 and incubate at 4 deg C. overnight. Wash latex particles in 0.1% tween in PBS and resuspend in same at 0.5% solids. Store at 4 deg C. in dark until use.

Paramagnetic Particle Binding to Antibody 1H12 using EDC

Incubate 1% paramagnetic particles with 20 mg/ml EDC and 20 mg/ml sulfo-NHS, all in 50 mM MES buffer, pH 6.0 for 20 min at room temperature with gentle shaking. Wash with PBS and resuspend in same at 1% solids.

Incubate 0.5% paramagnetic particles-EDC with 0.5 mg/ml 1H12, all in PBS, pH7.2, for 2h 15 min at room temperature.

Wash in 0.1% tween in 50 mM tris buffer at pH 7.1 and incubate at 4 deg C. overnight. Wash in 0.1% tween in PBS and resuspend in same to give 0.5% solids. Store at 4 deg C. until use.

Assay Procedure

Assay reagents were added to an eppendorf tube in the following volumes and concentrations:

| | |
|---|---|
| 1% paramagnetic particles (with bound 1H12): | 1 ul |
| 0.5% Latex (with GOD and 5A6 bound): | 1 ul |
| PSA (5x final concentration in 60 mg/ml BSA in PBS): | 2 ul |
| 1M glucose: | 1 ul |

All reagents added to eppendorf separately and kept separate in tube. All reagents finally combined by mixing upon addition of the:

| | |
|---|---|
| Reaction buffer: | 5 ul |

(Reaction buffer comprises 1M MES, pH 6.0, 2 mg/ml trehalose, 120 mg/ml BSA, 4 mg/ml HRP, 200 mM ferrocyanide)

These reagents are mixed thoroughly then 0.8 ul is added to a cartridge, which is connected up to a potentiostat (Autolab PGSTAT12). The cartridge is made up of a single channel spanned by 2 screen-printed carbon electrodes (one working electrode and one counter/reference electrode) as shown in FIGS. 3 and 4. Measurements were carried out as follows:

Experimental Methodology

A pulsed electrochemical methodology was used to measure the anti-PSA-GOD label before and after the magnetic separation step. A chronoamperometric measurement was made every minute for a total of 8 minutes. Specifically a 0.1 sec chronoamperometric measurement at −350 mV was performed; the current value at the 0.1 seconds was recorded from the 0.1 second transient. After the application of the sample to the strip the binding and enzymatic reactions are simultaneously occurring. The pulsed electrochemical measurements are then performed every 1 minute and the data recorded. After 4 minutes the magnetic field is applied to the strip and the anti-PSA magnetic particles are removed from the working electrode. The removed anti-PSA magnetic particles will be a mixed population of anti-PSA magnetic with bound anti-PSA-GOD label via PSA and anti-PSA magnetic particles (with no label bound). The pulsed electrochemical measurements for 5, 6, 7 and 8 minutes constitute the measurement of the remaining unbound anti-PSA-GOD label. The 2, 3 and 4 minute currents values were used to calculate a slope by plotting Time (mins) vs. Current (amps) and fitting a linear regression. This slope constitutes the pre magnetic separation measurement.

The same methodology was applied to the 5, 6, 7 and 8 minute data. The resultant slope constitutes the post magnetic separation measurement as is a measure of the unbound anti-PSA-GOD label.

Results and Discussion

Figure 26:
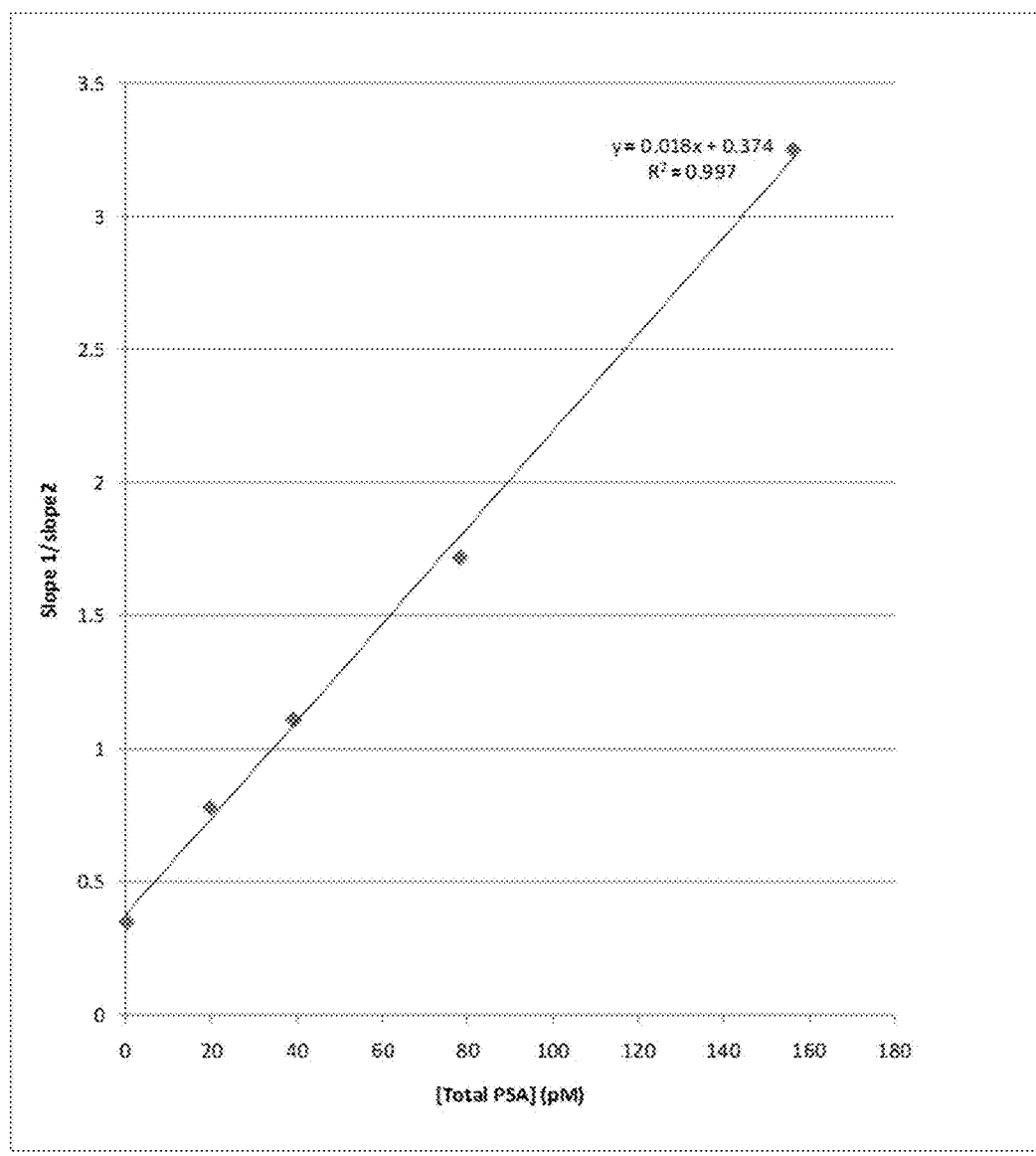
FIG. 26 shows a graph of PSA concentration measured by dividing the pre magnetic separation measurement slope by the post magnetic separation measurement slope, in accordance with the current invention.

The ratio of the pre magnetic separation slope divided by the post magnetic measurement was then plotted against Total PSA concentration (pM) as shown in FIG. 26. A systematic linear response is observed, with high sensitivity.

What is claimed is:

1. A method of determining the concentration of an analyte in a liquid sample, the method comprising:
   (a) combining the sample with (i) an analyte binding agent that binds the analyte and (ii) a label for use in detecting the analyte, so that the analyte binding agent, the analyte, if present in the sample, and the label form an analyte binding agent/analyte/label complex;
   (b) detecting a total level of the label present in a detection area, wherein the label is present in the analyte binding agent/analyte/label complex or is uncomplexed, to provide a first reference value;
   (c) removing any binding agent/analyte/label complex from the detection area;
   (d) detecting a level of any uncomplexed label and unreacted label that remains in the detection area after removal of the analyte binding agent/analyte/label complexes; and
   (e) determining the concentation of the analyte present in the sample, if any, by subtracting the level of uncomplexed/unreacted label from the first reference value.

2. The method according to claim 1, wherein the detection is performed directly on the sample, without any separation, washing step, or dilution of the sample.

3. The method according to claim 1, wherein the detection is carried out electrochemically.

4. The method according to claim 3, wherein an oxidising or reduction potential is used to measure a level of label.

5. The method according to claim 4, wherein a potential is applied to reduce background effects caused by an electrochemical interferent that may be present in the sample.

6. The method according to claim 3, wherein the label is glucose oxidase.

7. The method according to claim 6, further comprising a peroxidase and a mediator that can be converted between oxidised and reduced forms that can be electrochemically detected.

8. The method of claim 7, wherein the peroxidase is horseradish peroxidase.

9. The method of claim 7, wherein the mediator is ferrocyanide or ABTS.

10. The method according to claim 1, wherein the binding agent is coupled to a particle capable of forming a complex with analyte present in the sample that can be removed, when complexed or uncomplexed with analyte from the detection area.

11. The method according to claim 10, wherein the particle is a paramagnetic particle that can be removed by a magnet or electromagnet.

12. The method according to claim 1, wherein the sample is a sample of whole blood.

* * * * *